United States Patent [19]

Jones et al.

[11] 4,423,070

[45] Dec. 27, 1983

[54] ESTERS

[75] Inventors: Geraint Jones; John Preston; David S. Thomson, all of Macclesfield, England

[73] Assignee: Imperial Chemical Industries Limited, London, England

[21] Appl. No.: 855,004

[22] Filed: Nov. 23, 1977

[30] Foreign Application Priority Data

Dec. 16, 1976 [GB] United Kingdom ............... 52553/76
Sep. 30, 1977 [GB] United Kingdom ............... 40773/77

[51] Int. Cl.$^3$ ...................... C07C 69/14; C07C 69/16; A61K 31/22
[52] U.S. Cl. ..................................... 424/311; 560/138
[58] Field of Search ........................ 560/138; 424/311

[56] References Cited

U.S. PATENT DOCUMENTS 3,933,911  1/1976  Main ..................................... 260/562
3,957,870  5/1976  Main ..................................... 260/562

FOREIGN PATENT DOCUMENTS 809831  7/1974  Belgium .
1298711  12/1972  United Kingdom .

Primary Examiner—Dolph H. Torrence
Assistant Examiner—C. Joseph Foraci
Attorney, Agent, or Firm—Cushman, Darby & Cushman

[57] ABSTRACT

The invention concerns di- and tri-esters derived from alkanoic, (cycloalkyl)alkanoic, benzoic or phenylalkanoic acids with N-(acylaminoalkyl)-dihydroxyphenylethanolamines, and pharmaceutically acceptable salts thereof; processes for their preparation and manufacture; and pharmaceutical compositions thereof. The esters are useful for the topical treatment of an area of inflammation affecting the skin of a warm-blooded animal. Representative esters of the invention are 1-[3,4-bis(pivaloyloxy)phenyl]-2-[2-(2-phenylacetamido)ethylamino]-ethanol, 1-[3,4-bis(pivaloyloxy)phenyl]-2-[1,1-dimethyl-2-(2-phenoxyacetamido)-ethylamino]-ethanol, and the hydrochlorides and hydrobromides thereof.

5 Claims, No Drawings

ESTERS

This invention relates to new esters and, in particular it relates to new esters of phenylethylamines which possess anti-inflammatory activity when applied topically to an area of inflammation.

According to the invention there is provided an ester of the formula:

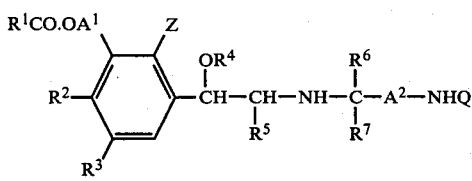

wherein $R^1$ is a $C_{1-11}$-alkyl or $(C_{3-6}$-cycloalkyl$)$-$C_{1-5}$-alkyl radical, or a phenyl or benzyl radical optionally bearing a $C_{1-6}$-alkyl or $C_{1-6}$alkoxy radical as a nuclear substituent; one of $R^2$ and $R^3$ is hydrogen; the other of $R^2$ and $R^3$ is a radical of the formula $R^1CO.O$—wherein $R^1$ has the meaning stated above; $R^4$ is hydrogen, a $C_{2-12}$-alkanoyl or $(C_{3-6}$-cycloalkyl$)$-$C_{2-6}$-alkanoyl radical, or a benzoyl or phenyl acetyl radical optionally bearing a $C_{1-6}$-alkyl or $C_{1-6}$-alkoxy radical as a nuclear substituent $R^5$ is hydrogen or a methyl radical; $R^6$ and $R^7$, which may be the same or different are hydrogen, or $C_{1-6}$-alkyl radicals; $A^1$ is a direct bond or a methylene radical; $A^2$ is a $C_{1-4}$-alkylene radical; Z is hydrogen or chlorine and Q is a radical of the formula:

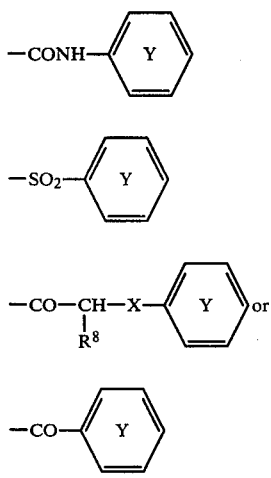

wherein $R^8$ is hydrogen or a methyl radical, X is a direct bond or oxygen, and benzene ring Y optionally bears a halogen atom, or trifluoromethyl, $C_{1-6}$-alkyl or $C_{1-6}$-alkoxy radical as a substituent, or a pharmaceutically acceptable acid-addition salt thereof.

A particular value for $R^1$ when it is a $C_{1-11}$-alkyl radical is, for example, a straight chain $C_{1-11}$-alkyl radical, for example a methyl, ethyl, propyl, butyl, pentyl, hexyl or heptyl radical, or a branched chain $C_{3-11}$-alkyl radical, for example an isopropyl, isobutyl, t-butyl, 1-methyl-2,2-dimethylpropyl, 2,2-dimethylpropyl, 1-ethylpropyl or 1,1-diethylpropyl radical; of which values isopropyl, isobutyl and t-butyl are particularly preferred.

A particular value for $R^1$ when it is a $(C_{3-6}$-cycloalkyl$)$-$C_{1-5}$-alkyl radical is, for example, a (cyclopentyl)methyl radical.

A particular value for $R^4$ when it is a $C_{2-12}$-alkanoyl radical is, for example, such a radical of the formula Alkyl.CO—wherein Alkyl has any of the particular values for $R^1$ stated above when it is a $C_{1-11}$-alkyl radical.

A particular value for $R^4$ when it is a $(C_{3-6}$-cycloalkyl$)$ $C_{2-6}$-alkanoyl radical is, for example, a (cyclopentyl)acetyl radical.

A particular value for $R^6$ or $R^7$ when it is a $C_{1-6}$-alkyl radical is, for example, a methyl or ethyl radical.

A particular value for $A^2$ is, for example, a methylene or ethylene radical.

A particular value for a $C_{1-6}$-alkyl or $C_{1-6}$-alkoxy radical, when present as an optional substituent on benzene ring Y, or as an optical nuclear substituent when $R^1$ is a phenyl or benzyl radical, or when $R^4$ is a benzoyl or phenylacetyl radical is, for example, a methyl or methoxy radical.

A particularly suitable value for the radical $R^1CO$—when $A^1$ is a direct bond is, for example, a pivaloyl, isobutyryl or isovaleryl radical, and when $A^1$ is a methylene radical is, for example, an acetyl radical.

A particular value for a halogen atom when present as an optional substituent on benzene ring Y is, for example, a fluorine, chlorine or bromine atom.

A particular value for ring Y is, for example, a phenyl, halogenophenyl, $C_{1-6}$-alkoxyphenyl, trifluoromethylphenyl or $C_{1-6}$-alkylphenyl radical, for example a 4-chloro-, 4-fluoro-, 4-methoxy-, 3-trifluoromethyl- or 4-methyl-phenyl radical.

A particularly suitable value for Q when it is a radical of formula II is, for example, an N-phenylcarbamoyl or N-(p-chlorophenyl)carbamoyl radical.

A particularly suitable value for Q, when it is a radical of formula III, is, for example, a phenylsulphonyl or toluene p-sulphonyl(tosyl) radical.

A particularly suitable value for Q, when it is a radical of formula IV and X is a direct bond, is, for example, a phenylacetyl, 4-fluoro-, 4-chloro- or 4-methoxyphenylacetyl or 2-phenylpropionyl radical.

A particularly suitable value for Q, when it is a radical of formula IV and X is oxygen, is, for example, a phenoxyacetyl or (3-trifluoromethylphenoxy)acetyl.

A particularly suitable value for Q, when it is a radical of the formula V, is, for example a benzoyl, 4-chlorobenzoyl, 4-methylbenzoyl or 4-methoxybenzoyl radical.

It will be appreciated that various particular and individual groups of esters of the invention are comprised within the above general definition, namely those esters of formula I, or acid-addition salts thereof, wherein one of the radicals $R^1$, $R^2$, $R^3$, $R^4$, $R^5$, $R^6$, $R^7$, $R^8$, $A^1$, $A^2$, Z and Q has one of the above defined particular values, and the remainder of the said radicals have any of the above defined general or particular values. However, specific groups of esters of the invention which are of particular interest comprise those compounds of formula I wherein:

(a) $R^2$ is a radical of the formula $R^1CO.O$— and $R^3$ is hydrogen;

(b) $R^2$ is hydrogen and $R^3$ is a radical of the formula $R^1CO.O$—;

(c) $A^1$ is a direct bond;

(d) $A^1$ is a methylene radical;

(e) Z is hydrogen; or (f) Z is chlorine; and in each case the remainder of $R^1$, $R^2$, $R^3$, $R^4$, $R^5$, $R^6$, $R^7$, $R^8$, $A^1$, $A^2$, Z and Q have any of the above general or particular values; together in each case with the pharmaceutically acceptable acid-addition salts thereof.

Yet further particular groups of esters of the invention are comprised by those compounds of formula I defined in any of the above mentioned groups taken alone or in combination; and wherein, in addition $R^4$ and $R^5$ are both hydrogen; $R^6$ and $R^7$ are both hydrogen or methyl radicals; $A^2$ is a methylene radical; and Q is a radical of formula IV as defined above, preferably a phenylacetyl, phenoxyacetyl or 2-phenylpropionyl radical.

A particularly preferred group of esters of the invention comprises those compounds of formula I as defined by above groups (a) and (c) taken together, wherein in addition $R^1$ is an isopropyl, t-butyl, isobutyl or (cyclopentyl)methyl radical; $R^4$ and $R^5$ are both hydrogen; $R^6$ and $R^7$ are both hydrogen or methyl radicals; $A^2$ is a methylene radical; and Q is a phenylacetyl, phenoxyacetyl or 2-phenylpropionyl radical.

A particular acid-addition salt of an ester of formula I is such a salt derived from an acid affording a pharmaceutically acceptable anion, for example from an inorganic acid, for example hydrochloric, hydrobromic, phosphoric or sulphuric acid, or from an organic acid, for example oxalic, tartaric, lactic, fumaric, citric, acetic, salicylic, benzoic, β-naphthoic, methane sulphonic or adipic acid.

It will be observed that an ester of formula I possesses at least one asymmetric carbon atom i.e. that bearing the radical —$OR^4$, and can therefore exist in racemic and optically-active forms. In addition, depending on the nature of the substituents $R^5$, $R^6$, $R^7$ and $R^8$ an ester of the formula I may possess up to three additional asymmetric carbon atoms and can exist in the corresponding additional racemic and optically-active forms. It is to be understood that this invention encompasses the racemic forms of such an ester and any optically-active form which possesses anti-inflammatory activity, it being well known how a racemic form may be resolved into its optically-active forms, or how such optically-active form may be obtained by synthesis from optically-active starting materials, and how the pharmacological properties may be determined by the standard tests hereinbelow.

Specific esters of formula I are described hereinafter in the Examples, but of these the following are particularly preferred:

1-[3,4-bis(pivaloyloxy)phenyl]-2-[2-(2-phenylacetamido)ethylamino]-ethanol;
1-[3,4-bis(pivaloyloxy)phenyl]-2-[1,1-dimethyl-2-(2-phenylacetamido)ethylamino]-ethanol;
1-[3,4-bis(pivaloyloxy)phenyl]-2-[1,1-dimethyl-2-(2-phenoxyacetamido)-ethanol;
1-[3,4-bis(pivaloyloxy)phenyl]-2-[2-(2-phenoxyacetamido)ethylamino]-ethanol;
1-[3,4-bis(isovaleryloxy)phenyl]-2-[2-(2-phenylacetamido)ethylamino]-ethanol;
1-[3,4-bis(3,3-dimethylbutyryloxy)phenyl]-2-[2-(2-phenylacetamido)ethylamino]-ethanol;

and the pharmaceutically acceptable acid-addition salts thereof.

The esters of the invention may be manufactured by any chemical process known to be useful for the manufacture of chemically-analogous compounds. Such processes are provided as a further feature of the invention and comprise assembling in sequence by generally known chemical procedures the following five radicals, in which $R^1$, $R^2$, $R^3$, $R^4$, $R^5$, $R^6$, $R^7$, $A^1$, $A^2$ and Z have the meaning stated above:

(i) a 2-phenylethyl radical of the formula:

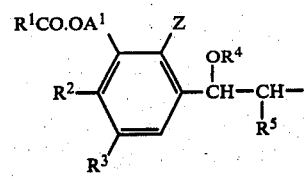

(ii) a first imino radical (—NH—);
(iii) a radical of the formula:

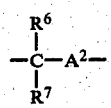

(iv) a second imino radical (—NH—); and
(v) a radical—Q.

The various stages of the assembly of an ester of the invention may be carried out in any possible order using known chemical processes for the synthesis of analogous compounds and, in particular, the introduction of the acyl groups $R^1CO$— and $R^4$, when it is other than hydrogen, may be carried out early in the synthesis or as a final step.

The following processes are given as particular, non-limiting, examples of such sequential chemical synthesis, wherein $R^1$, $R^2$, $R^3$, $R^4$, $R^5$, $R^6$, $R^7$, $R^8$, $A^1$, $A^2$, Q, X, Z and ring Y have the meanings stated above unless specifically stated otherwise:

(a) A compound of the formula:

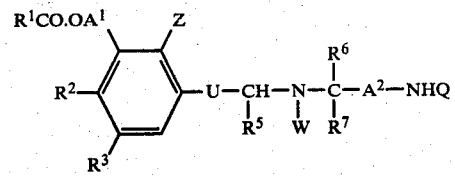

or an acid-addition salt thereof, wherein U is a carbonyl radical or a radical of the formula —$CHOR^4$— and W is a reductively removable protecting group, is reduced.

A particularly suitable reductively removable protecting group is, for example, a benzyl radical or a substitute benzyl radical, for example, a 4-methylbenzyl radical. As will be appreciated, the reduction must be carried out under conditions which do not result in reduction of carboxylic ester groups, and is therefore preferably carried out by means of catalytic hydrogenation, for example with hydrogen in the presence of a palladium (which is preferred) platinum or nickel catalyst, in a diluent or solvent, for example ethanol or water, or a mixture thereof. The reduction is conveniently carried out at, for example, 15°–30° C. and, may optionally be carried out under a pressure of hydrogen of, for example, up to 5 Kg./cm².

It is to be understood that the conditions necessary for removal of the protecting group W in the above process, also result in the reduction of a carbonyl radical U when present in the starting material of formula VIII, so that an ester of formula I wherein $R^4$ is hydrogen is thus obtained in such a case.

The starting materials of formula VIII wherein U is a radical of the formula —CH.OH— may be obtained, for example, by sodium borohydride reduction of the corresponding aryl ketone of the formula:

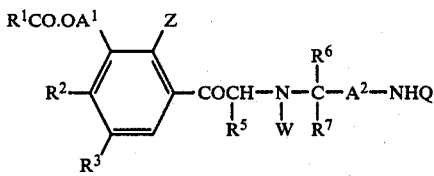   IX wherein W has the meaning defined above, using similar reduction conditions to those described hereinbelow in process (e). Such starting materials of formula VIII may conveniently be prepared and used in process (a) in the same vessel without the need for isolation and purification.

The aryl ketones of formula IX (which are also starting materials of formula VIII wherein U is a carbonyl radical) may themselves be prepared by reaction of an appropriate phenacyl halide of the formula:

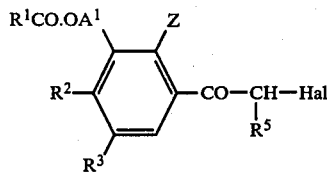   X wherein Hal is a halogen atom with an amino compound of the formula:

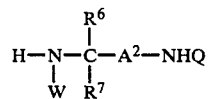   XI wherein W has the meaning defined above.

This reaction is conveniently carried out at or near normal room temperature, for example at 15° to 30° C., and in a diluent or solvent, for example ethanol, dioxan or acetonitrile. It may also be carried out in the presence of an acid-binding agent, for example an alkali metal carbonate or bicarbonate or an excess of amino compound XI. A particularly suitable value for Hal. is a chlorine or bromine atom. The amino compound of formula XI may be obtained by selective acylation of a diamine of the formula:

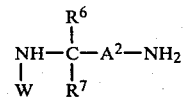   XII with an acylating agent derived structurally from an acid of the formula Q.OH, using known general procedures. Alternatively those starting materials of formula XI wherein W is a benzyl radical may be obtained by reductive alkylation of an amine of the formula:

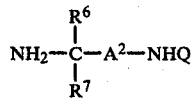   XIII by reaction with benzaldehyde in the presence of a suitable reducing agent, for example sodium borohydride, under conditions similar to those described for process (e) below.

The phenacyl halides of formula X may themselves be obtained by conventional side-chain halogenation of the appropriate acyl benzene of formula X but wherein Hal. is replaced by hydrogen, for example, as illustrated in Example 1 and 9 hereinafter.

Alternatively, the aryl ketones of formula IX may conveniently be obtained by acylation of a dihydroxy compound of the formula:

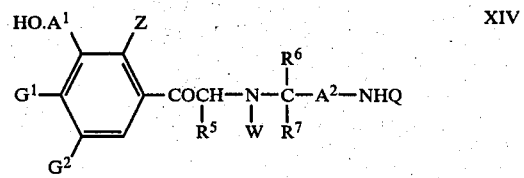   XIV wherein W has the meaning defined above, and one of $G^1$ and $G^2$ is hydrogen and the other is a hydroxy radical with an acylating agent structurally derived from an acid of the formula $R^1.CO_2H$, for example a chloride or bromide of such an acid, for example as illustrated in Example 7 and 8 hereinafter. The necessary dihydroxy compounds of formula XIV may themselves be obtained, for example, by acidic hydrolysis of a corresponding di-O-acetyl derivative (itself obtained by analogous processes to those described herein for esters of formula I), as illustrated hereinafter in Example 8.

The remaining starting materials of formula VIII, wherein U is a radical of the formula —$CHOR^9$—, but wherein $R^9$ has the same meaning as $R^4$ other than hydrogen, may be obtained by acylation of the corresponding compound of formula VIII wherein U is a radical of the formula—CH.OH—, by reaction with an acylating agent, for example an acid chloride, derived from an acid of the formula $R^9.OH$, wherein $R^9$ has the meaning defined above, using the general conditions specified in process (c) hereinbelow.

(b) For an ester of the formula I wherein $R^4$ is hydrogen, an aryl ketone of the formula:

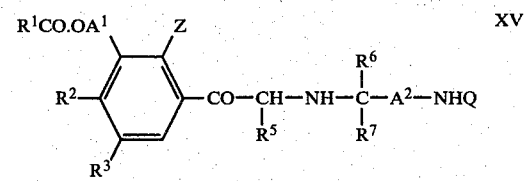   XV is reduced.

The reduction may be carried out by means of any agent generally known for reducing aromatic ketones, but which does not reduce carboxylic ester groups. Thus the reduction may be carried out by means of an alkali metal borohydride, for example sodium borohydride, in an inert diluent or solvent, for example methanol, ethanol or 2-propranol, which means is preferred, or by means of catalytic hydrogenation, for example with hydrogen in the presence of a palladium, platinum or nickel catalyst, in a diluent or solvent, for example ethanol or acetic acid, and in either case, at a temperature of, for example, −20° C. to 30° C., and conveniently, at or near normal room temperature, for example at 15° to 30° C.

The starting materials of formula XV may be obtained in an analogous manner to those of formula IX in process (a) hereinabove, by reaction of a phenacyl halide of formula X with the appropriate amino compound of formula XI but wherein W is hydrogen. The necessary amino compound may be obtained by selective acylation of a diamine of formula XII, but wherein W is hydrogen, for example as illustrated in the accompanying Examples.

Alternatively, the starting materials of formula XV may conveniently be obtained in an analogous manner to those of formula IX in process (a) hereinabove, by acylation of a dihydroxy compound of formula XIV, but wherein W is replaced by hydrogen, preferably in the presence of a strong acid to minimise any tendency for N-acylation, for example by using the dihydroxy compound as its hydrochloride, hydrobromide or trifluoroacetate salt. The necessary dihydroxy compounds may be obtained from the corresponding di-O-acetyl derivatives as described in (a) hereinabove, or by hydrogenolysis of the corresponding di-O-benzyl derivatives as illustrated in Example 7 hereinafter.

(c) For an ester of formula I wherein $R^4$ is hydrogen or an acyl radical of the formula $R^1.CO—$, a hydroxy compound of the formula:

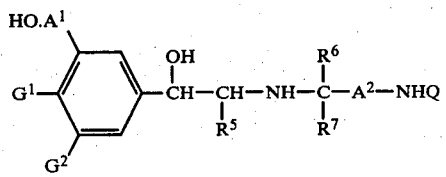

XVI wherein one of $G^1$ and $G^2$ is hydrogen and the other is a hydroxy radical, is reacted with an acylating agent derived structurally from an acid of the formula $R^1.CO_2H$.

The reaction is preferably carried out using an acid-addition salt of a compound of formula XVI for example a hydrogen halide salt for example a hydrogen chloride or hydrogen bromide, or a trifluoro acetate salt, so that N-acylation is thereby minimised.

A particularly suitable acylating agent derived structurally from one of the above-mentioned acids is, for example, an acid halide, for example an acid chloride or bromide, an anhydride, or a mixed anhydride with formic acid.

The reaction may be conveniently carried out in the presence of an inert diluent or solvent, for example acetone, acetonitrile, chloroform, methylene chloride, tetrahydrofuran, acetic acid or trifluoroacetic acid and conveniently, at a temperature, for example, of from 0° to 100° C.

It is to be understood that the quantity of acylating agent employed in the above process necessarily depends on the number of acyl radicals to be incorporated. Thus, when a compound of formula I wherein $R^4$ is a radical of the formula $R^1CO—$ is required, that is a triester, the above acylation is generally carried out using an excess of acylating agent at a temperature in the range, for example, 60°–100° C.

By contrast, when a compound of formula I wherein $R^4$ is hydrogen is required, that is a diester, the above acylation is generally carried out using a stoichiometric amount of acylating agent and at a temperature in the range, for example, 0° to 60° C., and preferably at or near normal temperature, for example at from 15° to 30° C.

The starting materials of formula XVI may be made by reduction of an acetophenone derivative of formula XIV wherein W is a benzyl radical with sodium borohydride in 2-propanol, followed by catalytic hydrogenolysis of the benzyl radical using a similar procedure to that described in process (a) hereinabove. Alternatively, they may be obtained by conventional acidic or basic hydrolysis of an ester of formula I, for example wherein $R^1$ is a methyl radical and $R^4$ is hydrogen, conveniently in an alcohol, for example methanol, and at a temperature of 15°–60° C. As a yet further alternative, a di-O-benzyl ether of general formula I, but wherein the radical $R^1CO—$ is replaced by a benzyl radical, and $R^4$ is hydrogen, is catalytically hydrogenolysed, for example as illustrated in Example 17 hereinafter.

(d) For an ester of formula I wherein $R^4$ is other than hydrogen, a compound of formula I wherein $R^4$ is hydrogen is reacted with an acylating agent derived structurally from an acid of the formula $R^9.OH$ wherein $R^9$ has the same meaning as $R^4$ other than hydrogen.

A particularly suitable acylating agent derived structurally from an acid of formula $R^9.OH$ is, for example, an acid halide, for example an acid chloride or bromide, an acid anhydride, or a mixed anhydride with formic acid.

The reaction may be carried out under the same general conditions as specified in (c) hereinabove.

(e) For an ester of formula I wherein $R^4$ is hydrogen, a carbonyl derivative of the formula:

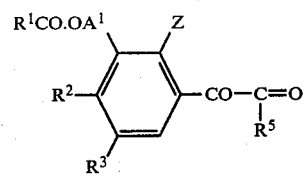

XVII is condensed with an amine of the formula:

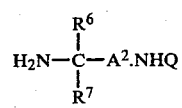

XIII under reducing conditions.

Particularly suitable reducing conditions are provided by using, for example, an alkali metal borohydride or cyanoborohydride, for example sodium borohydride or cyanoborohydride, of which a cyanoborohydride is particularly preferred, conveniently in an inert solvent or diluent, for example acetonitrile, methanol, ethanol or 2-propanol and at a temperature in the range, for example, −20° to 30° C. When sodium cyanoborohydride is used, the reaction is preferably carried out at or near pH 4, for example in the presence of acetic acid.

It will be appreciated that processes of the above general type are known as reductive alkylations, and proceed at least in part through an intermediate of the formula:

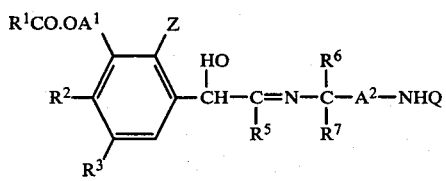 XVIII (the —N=CR⁵— bond of which is subsequently reduced), and/or of the formula:

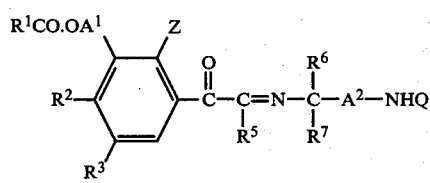 XIX (the —N=CR⁵— and ketone bond of which are subsequently reduced). Such an intermediate of formula XVIII or XIX (or a mixture thereof may be prepared and reduced in two separate stages in the above process if required.

The starting materials of formula XVII may be obtained by selenium dioxide oxidation of a compound of the formula:

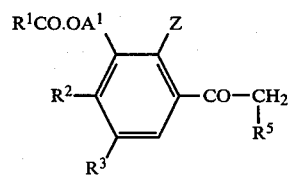 XX in an appropriate solvent, for example aqueous dioxan, optionally followed in the case of compounds of formula XVII wherein R⁵ is hydrogen by hydrate, acetal or hemiacetal formation, in which form, they may also be employed in the above process (e).

Those starting materials of formula XVII wherein R⁵ is hydrogen may conveniently also be obtained by dimethyl sulphoxide oxidation of the corresponding phenacyl bromide of the formula:

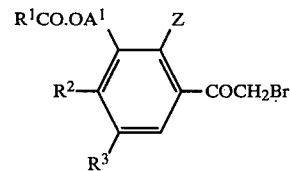 XXI under conventional conditions, for example as described in Example 13 hereinafter.

The phenacyl bromides of formula XXI may be made by analogy with those of formula X, or by transacylation as described in (f) hereinbelow.

(f) For an ester of formula I wherein R⁴ and R⁵ are both hydrogen; a compound of the formula:

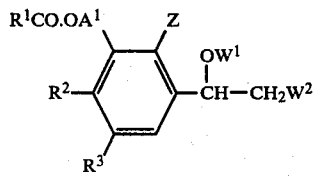 XXII wherein W¹ and W² together form a direct bond, or wherein W¹ is hydrogen and W² is a halogen atom, or a mixture of such compounds, is reacted with an amine of the formula XIII.

It will be appreciated that compounds of formula XXII wherein W¹ and W² together form a direct bond are ethylene oxide derivatives of the formula:

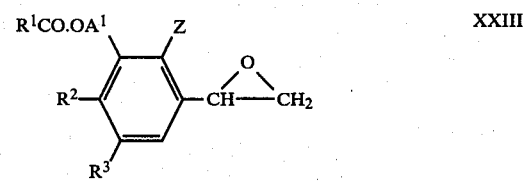 XXIII and that compounds of formula XXII wherein W¹ is hydrogen and W² is a halogen atom are halohydrins of the formula:

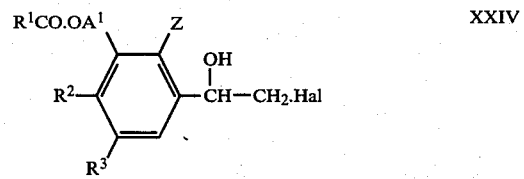 XXIV wherein Hal. is a halogen atom, for example, a chlorine, bromine or iodine atom; and that such compounds of formula XXIII or XXIV, or a mixture thereof, may be readily obtained by reduction, for example, using sodium borohydride or aluminium isopropoxide, of a phenacyl halide of the formula:

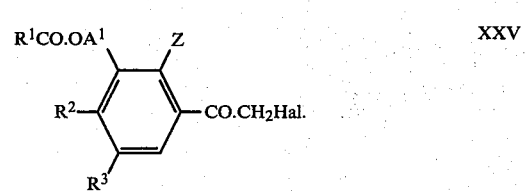 XXV wherein Hal. has the meaning stated above, with or without spontaneous dehydrohalogenation of the first formed halohydrin of formula XXIV.

The above process (f) may be carried out at ambient temperature or it may be accelerated or completed by application of heat, for example by heating to a temperature in the range 80° to 150° C.; it may be carried out at atmospheric or at an elevated pressure, for example by heating in a sealed vessel; and it may be carried out in an inert diluent or solvent, for example methanol, ethanol or 2-propanol.

The phenacyl halides of formula XXV may be made by analogous procedures to those used for the halides of formula X and XXI. Thus, they may be obtained by conventional side-chain halogenation of the appropriate acetophenone or by transacylation of a di-O-acetyl derivative of the formula:

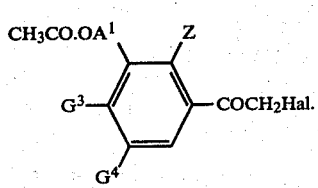

XXVI wherein one of $G^3$ and $G^4$ is an acetoxy radical and the other is hydrogen, and Hal. has the meaning stated above, by reaction with the sodium salt of the appropriate acid of formula $R^1.CO_2H$ at 150°–180° C., for example as illustrated in Example 14 hereinafter.

Optically-active forms of an ester of the invention may be obtained by conventional resolution of the corresponding racemic form of the ester of the invention.

The said resolution may be carried out by reacting a racemic form of an ester of formula I with an optically active acid, followed by fractional crystallisation of the diastereoisomeric mixture of salts thus obtained from a diluent or solvent, for example ethanol, whereafter the optically-active form of the ester of formula I is liberated by treatment under such conditions as avoid the hydrolysis of the ester, for example by anion exchange chromatography. A particularly suitable optically-active acid is, for example, (+)- or (−)-O,O-di-p-toluoyltartaric acid, or (−)-2,3:4,5-di-O-isopropylidene-2-keto-L-gulonic acid.

The ester of formula I in free base form may be converted into a pharmaceutically acceptable acid-addition salt by reaction with a suitable acid as defined hereinbefore and by conventional means which avoid hydrolysis of the ester. Alternatively, when a hydrogen chloride or bromide salt is required, this may be conveniently obtained by producing a stoichiometric amount of the hydrogen halide in situ by catalytic hydrogenation of the appropriate benzyl halide, preferably in an inert solvent or diluent, for example ethanol, and at, or near, room temperature.

The esters of formula I are conveniently used as their pharmaceutically acceptable acid-addition salts.

As stated above, the esters of formula I possess anti-inflammatory activity when applied topically to an area of inflammation and, in particular, are therefore useful in treating inflammatory diseases or inflammatory conditions of the skin, in warm-blooded animals.

The anti-inflammatory properties of an ester of formula I may be demonstrated in a standard test involving the inhibition of croton oil induced inflammation on the mouse ear. The activity of an individual ester of formula I in this test depends upon its particular chemical structure, but specific esters of formula I as described herein produced a significant inhibition of the inflammation at a topically applied dose of 0.30 mg. per ear, or less.

Another standard test in which the anti-inflammatory properties of an ester of formula I may be demonstrated involves the inhibition of oxazolone induced contact sensitivity on the mouse ear. Again the activity of a particular ester of formula I in this test depends on its particular chemical structure, but specific esters of formula I as described herein produced a significant inhibition of the inflammation at a topically applied dose of 0.6 mg. per ear, or less.

No overt toxic effects were detected at the active doses in either of the above tests.

In general, an ester of formula I may be used in the treatment of inflammatory diseases or inflammatory conditions of the skin in an analogous manner to that in which known topically active anti-inflammatory agents, for example the topically active steroids, are used.

When used for the topical treatment of an area of inflammation affecting the skin of a warm-blooded animal, for example man, an ester of formula I may be administered topically at a dose in the range 10 µg. to 15 mg./cm²., or at an equivalent dose of a pharmaceutically acceptable acid-addition salt thereof, and, if necessary, a dose in this range is repeated at intervals of, for example, 4–12 hours. It will be appreciated that the total daily amount of an ester of formula I administered depends on the extent and severity of the inflammation under treatment.

By way of example, when 1-[3,4-bis(pivaloyloxy)phenyl]-2-[1,1-dimethyl-2-(2-phenoxyacetamido)ethylamino]-ethanol is used for the topical treatment of an area of inflammation affecting the skin of a warm-blooded animal, for example man, a dose in the range 1 µg. to 5 mg./cm²., or an equivalent amount of a pharmaceutically acceptable acid-addition salt thereof, is administered topically, and if necessary, is repeated at intervals in the range 4–12 hours.

The esters of formula I may be administered in the form of pharmaceutical compositions and according to a further feature of the invention there is provided a pharmaceutical composition comprising an ester of formula I, or a pharmaceutically acceptable acid-addition salt thereof, in association with a pharmaceutically acceptable diluent or carrier, in a form suitable for topical administration, for example in the form of an ointment, gel, aqueous or oily solution or suspension, emulsion or aerosol formulation. A pharmaceutical composition according to this aspect of the invention may contain from 0.1% to 10% w/w of an ester of formula I or an equivalent amount of a pharmaceutically acceptable acid-addition salt thereof, hereinafter referred to as an active ingredient.

The pharmaceutical compositions may be made by methods well known in the art, using conventional pharmaceutically acceptable diluents or carriers.

A particular ointment formulation is prepared by dispersing an active ingredient as defined above in a suitable organic diluent, for example soft paraffin, optionally in the presence of an emulsifying and/or thickening agent, for example sorbitan monostearate.

A particular gel formulation is prepared by adding a gelling agent, for example carboxy-polymethylene, to a solution of an active ingredient as defined above in a suitable organic solvent, for example isopropyl alcohol.

A particular emulsion formulation, for example a cream or a lotion, is prepared by mixing an active ingredient as defined above with a suitable conventional emulsifying system and water.

A pharmaceutical composition according to this aspect of the invention may contain in addition to an active ingredient as defined above, at least one known pharmaceutical agent selected from: corticosteroids, for example fluocinolone acetonide, prednisolone, flumethasone pivalate, betamethasone valerate, hydrocortisone or dexamethasone; phosphodiesterase inhibitors, for example theophy line or caffeine; antibacterial agents, for example oxytetracycline, gentamicin, neomycin, gramicidin, chlorhexidine or cetyltrimethylammonium bromide; anti-fungal agents, for example griseofulvin or nystatin; antihistamines, for example diphenhydramine or chlorphenamine; local anaesthetics, for example amylocaine, benzocaine or procaine; and emollients, for example calomine. In addition the compositions may also contain conventional excipients such as colours, chelating agents or preservatives as desired.

The invention is illustrated but not limited by the following Examples in which:
(i) unless otherwise stated, all procedures were carried out at room temperature (in the range 18°–26° C.) and at atmospheric pressure; and all evaporations were performed by rotary evaporation under reduced pressure;
(ii) infra-red (IR) spectroscopic data, where given, is presented in the form of absorbance values ($\nu$max.) for characteristic radicals;
(iii) nuclear magnetic resonance (NMR) data, where given, is presented in the form of chemical shifts ($\delta$values) for characteristic protons, relative to tetramethyl silane (TMS) as standard determined in $d_6$-DMSO as solvent (unless stated otherwise) and at 100 MHz; and
(iv) yields, where given, are purely illustrative and are not to be construed as the maximum attainable.

EXAMPLE 1

A solution of 2-{N-benzyl-N-[2-(2-phenylacetamido)ethyl]amino}-3',4'-bis(pivaloyloxy)acetophenone hydrobromide (2.5 g.) in a mixture (50 ml.) containing 70% v/v of ethanol in water was hydrogenated for 18 hours at a pressure of 3.5 kg./cm² at room temperature using 10% palladium-carbon (0.8 g.). The catalyst was separated by filtration and the filtrate evaporated. Trituration of the residue with ether (30 ml.) containing several drops of ethanol gave 1-[3,4-bis(pivaloyloxy)phenyl]-2-[2-(2-phenylacetamido)ethylamino]ethanol as its hydrobromide (1.7 g.) m.p. 111°–113° C. (hemi-hydrate).

The starting acetophenone derivative was obtained as follows:

A solution of 2-bromo-3',4'-bis(pivaloyloxy)acetophenone (2.63 g.) and N-[2-(benzylamino)ethyl]-2-phenylacetamide (3.7 g. 2 molecular equivalents) in dioxan (20 ml.) was stirred overnight at room temperature.

The reaction mixture was diluted with dry ether (200 ml.) and a precipitate of N-[2-(benzylamino)ethyl]-2-phenylacetamide hydrobromide was separated. The ethereal solution was washed with water (3×50 ml.) and brine (100 ml.), dried (MgSO₄) and filtered. A fresh solution of saturated ethereal hydrogen bromide was then added to the filtrate until the solution was just acid. After 18 hours at 0°–5° C. the precipitate was collected to give 2-[N-benzyl-N-[2-(2-phenylacetamido)ethyl]amino]-3',4'-bis(pivaloyloxy)acetophenone hydrobromide as a crude solid. Crystallisation of a portion of the crude solid from ethylacetate gave analytically pure material having m.p. 176°–178° C.

The required 2-bromo-3',4'-bis(pivaloyloxy)acetophenone starting material was itself obtained as follows:

A suspension of 3,4-dihydroxy acetophenone (13.1 g., 0.08 mole) in chloroform (320 ml.) was cooled in an ice bath to 0°–5° C. A solution of pivaloyl chloride (19.2 ml., 0.16 mole) in chloroform (80 ml.) and a solution of triethylamine (22.2 ml., 0.16 mole) in chloroform (80 ml.) were added dropwise simultaneously to the stirred suspension during 10 minutes. The reaction mixture was stirred at 0°–5° C. for a further 1 hour and then was poured into a mixture of 2N-hydrochloric acid (100 ml.) and ice (200 g.). The mixture was extracted with chloroform (3×150 ml.), and the extracts washed successively with water (100 ml.), 10% w/v sodium carbonate solution (100 ml.), water (100 ml.) and brine (100 ml.). After drying (MgSO₄) the combined extracts were evaporated to give crude 3,4-bis(pivaloyloxy)acetophenone as an oil (23.1 g.) which was used without purification.

A solution of bromine (3.15 ml., 0.061 mole) in chloroform (50 ml.) was added dropwise at room temperature to a stirred solution of 3',4'-bis(pivaloyloxy)acetophenone (19.5 g., 0.061 mole) and t-butyl acetate (8.2 ml., 0.06 mole) in chloroform (150 ml.) containing a catalytic amount of anhydrous aluminium chloride (0.2 g.). The reaction mixture was stirred at room temperature for 1 hour after the addition was complete, chromatographic silica gel (75 g.) was then added and the mixture evaporated in vacuo. The residual solid was added to the top of a column of dry chromatographic silica-gel (1 kg., previously deactivated by addition of 10% w/w water and then equilibrated with 10% v/w of a 5% v/v solution of ethyl acetate in toluene). The column was developed by elution with a 5% v/v solution (1.1 l.) of ethyl acetate in toluene. The column was then eluted with ethyl acetate (2×500 ml.) and the fractions collected were monitored by thin layer chromatography (TLC) (on silica plates developed in a 50% v/v mixture of ethyl acetate and toluene). The later fractions were combined and evaporated to give 2-bromo-3',4'-bis(pivaloyloxy)acetophenone as an oil (14.2 g.) which rapidly crystallised to give a solid of m.p. 64°–66° C.

The starting phenylacetamide derivative was itself prepared as follows:

A mixture of ethyl phenyl acetate (100 g., 0.61 mole) and ethylene diamine (120 ml., 1.86 moles) was heated on a stream bath for 4 days. Excess ethylene diamine was removed under reduced pressure and the residue dissolved in water (500 ml.) and any insoluble material was removed by filtration. Evaporation of the filtrate gave crude N-(2-aminoethyl)-2-phenylacetamide (96.8 g.) which was used without purification.

Benzaldehyde (67.5 g., 0.637 mole) was added to a solution of N-(2-aminoethyl)-2-phenylacetamide (113.5 g., 0.637 mole) and the mixture was stirred at room temperature for 18 hours. Sodium borohydride (24.2 g.) was added in portions and the reaction mixture was stirred for an additional 1.5 hours. Acetic acid was then added until excess borohydride had been destroyed. The reaction mixture was basified by addition of 2 N sodium hydroxide solution and extracted with ethyl acetate (3×500 ml.). The extracts were washed with brine (300 ml.), dried (MgSO₄) and filtered. Hydrogen chloride gas was bubbled into the ethyl acetate filtrate until it was acid (pH~2). After 4 hours at 0° C., the precipitate was collected to give N-[2-(benzylamino)ethyl]-2-phenylacetamide hydrochloride (46.2 g.), m.p. 183°–185° C.

The free base was liberated from the hydrochloride (15 g.) by basification of a solution in water (150 ml.) with solid sodium carbonate. The aqueous mixture was extracted with ethyl acetate (3×100 ml.) and the extracts were dried (MgSO₄) and evaporated to give N-[2-(benzylamino)ethyl]-2-phenylacetamide as an oil (13.0 g.), which slowly crystallised.

EXAMPLE 2

A suspension of 2-{N-benzyl-N-[2-(2-phenylacetamido)ethyl]amino}-3',4'-bis(pivaloyloxy)acetophenone (2.0 g.) in 2-propanol (20 ml.) was cooled to −10° C. and sodium borohydride (0.34 g.) added in two portions interspersed by a portion of methanol (4 ml.). After 30 minutes at −10° C. a saturated aqueous solution (150 ml.) of sodium chloride (brine) was added and the mixture was extracted with ether (3×80 ml.). Evaporation of the dried (MgSO4) ethereal extracts gave 1-[3,4-bis(pivaloyloxy)phenyl]-2-[2-(2-phenylacetamido)-N-benzyl-ethylamino]ethanol (1.65 g.) which was dissolved without purification in ethanol (40 ml.). To this solution was added benzyl bromide (0.37 ml., 0.0031 mole) and the mixture was then hydrogenated in the presence of 10% palladium-carbon (0.4 g.) at atmospheric pressure and room temperature during 2 hours. The catalyst was separated, washed with ethanol (10 ml.) and the ethanol washings and reaction solution was evaporated together. The residue was triturated with ether (20 ml.) containing several drops of ethanol to give 1-[3,4-bis(pivaloyloxy)phenyl]-2-[2-(2-phenylacetamido)ethylamino]ethanol hydrobromide, (1.2 g.), m.p. 110°–115° C., identical with that obtained in Example 1.

EXAMPLE 3

A solution of 3',4'-bis(pivaloyloxy)phenylglyoxal (0.68 g., 0.002 mole) and N-(2-amino-2-methylpropyl)-2-phenylacetamide (0.41 g., 0.002 mole) in methanol (15 ml.) was stirred at room temperature for 18 hours. The reaction mixture was stirred and cooled to −10° C. and sodium borohydride (0.23 g., 0.003 mole) was added in portions. The mixture was further stirred at −10° C. for 45 minutes after the addition was complete. Brine (100 ml.) was then added and the mixture was extracted at room temperature with ether (3×60 ml.). After washing with brine (50 ml.) and drying (MgSO4), the ethereal extracts were evaporated to give 1-[3,4-bis(-pivaloyloxy)phenyl]-2-[1,1-dimethyl-2-(2-phenylacetamido)ethylamino]ethanol as an oil (0.64 g.). A solution of this oil in ethanol (15 ml.) was hydrogenated with benzylbromide (148 μl., 0.0012 mole) in the presence of 10% palladium-carbon (0.3 g.) at atmospheric pressure and room temperature during 2 hours. The catalyst was then separated by filtration, washed with ethanol (5 ml.) and the filtrate and washings evaporated. Trituration of the residue with ether (300 ml.) at 0° C. yielded 1-[3,4-bis(pivaloyloxy)phenyl]-2-[1,1-dimethyl-2-(2-phenylacetamido)ethylamino]ethanol hydrobromide in 48% yield. An analytically pure sample was obtained by crystallisation of the hydrobromide from water and had m.p. 134°–136° C.

The starting phenylglyoxal derivative was obtained as follows:

A solution of 2-bromo-3',4'-bis(pivaloyloxy)acetophenone (2 g.) in dimethyl sulphoxide (10 ml.) was allowed to stand for 18 hours at room-temperature, then poured into ice-water and extracted with ether (3×60 ml.). The ether solution was washed with water (50 ml.) and brine (50 ml.), dried (MgSO4) and evaporated to give 3',4'-bis(pivaloyloxy)phenylglyoxal as an oil (1.8 g.); νmax.: 1760 cm$^{-1}$ (ester >C═O), 1690 cm$^{-1}$ (—CO.CHO); δ(CDCl3): 8.2–7.1 (complex, aromatic —H), 1–35 (18H, singlet —C.CH3).

The starting N-(2-amino-2-methylpropyl)-2-phenylacetamide was obtained in a similar manner to that described for N-(2-aminoethyl)-2-phenylacetamide in Example 1 but using 1,2-diamino-2-methylpropane, and had m.p. 55°–59° C. (m.p. 68°–71° C., after crystallisation from aqueous ethanol).

EXAMPLE 4

The process described in Example 1 for 1-[3,4-bis(-pivaloyloxy)phenyl]-2-[2-(2-phenylacetamido)ethylamino]ethanol hydrobromide was repeated except that the appropriate 2-[N-benzyl-N-[2-(substituted amido)ethylamino]-3',4'-bis(acyloxy)acetophenone hydrobromide was hydrogenated. There were thus obtained in yields of 43–90% the following hydrobromides of compounds of the formula:

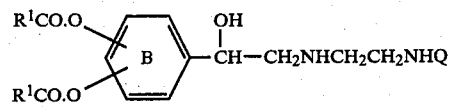

XXVII

| No. | Substituents position (Ring B) | R$^1$ | Q | Characteristic Properties |
|---|---|---|---|---|
| 1. | 3,4 | 2,2-dimethylpropyl | phenylacetyl | m.p. 141–142° C. (hydrate) |
| 2. | 3,5 | t-butyl | phenylacetyl | oil$^1$ |
| 3. | 3,5 | 2,2-dimethylpropyl | phenylacetyl | oil$^2$ |
| 4. | 3,5 | cyclopentylmethyl | phenylacetyl | oil$^3$ |
| 5. | 3,5 | t-butyl | benzoyl | m.p. 166–169° C. (hydrate) |
| 6. | 3,4 | t-butyl | (p-fluorophenyl)acetyl | m.p. 174–175° C. (hemi-hydrate) |

Notes:
$^1$NMR: (d$^6$-DMSO) 8.17δ (1H, —NHCO—), 7.2–6.7 (8H, complex, aromatic protons), 5.0δ (1H, broad singlet, —CHOH—), 3.4–2.6δ (complex, —CH2—), 1.1δ (18H, singlet, C—CH3).

$^2$NMR: (d$^6$-DMSO) 8.38δ (1H, —NHCO—), 7.4–6.7δ (8H, complex, aromatic protons), 5.0δ (1H, broad singlet, —CH.OH—), 3.7–2.6δ (complex, —CH2—), 2.45δ (4H, singlet, —CH2CO—), 1.06δ (18H, singlet, C—CH3).

$^3$NMR: (d$^6$-DMSO) 8.38δ (1H, —NHCO—), 7.4–6.75δ (8H, complex, aromatic protons), 5.0δ (1H, broad singlet, —CH.OH—), 3.9–2.7δ (complex, —CH2—), 2.5δ (4H, complex, —CH2CO—), 2.0–1.0δ (—CH2—, cyclopentyl ring).

The starting acetophenone hydrobromides were made in a similar manner to that described for 2-{N-benzyl-N-[2-(2-phenylacetamido)ethyl]amino}-3',4'-bis(pivaloyloxy)acetophenone hydrobromide in Example 1. There were thus obtained the following hydrobromides of acetophenone derivatives of the formula:

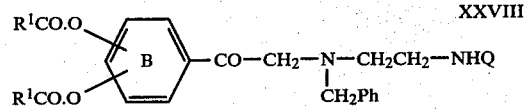

XXVIII

| No. | Substituents position (Ring B) | R$^1$ | Q | m.p. (°C.) |
|---|---|---|---|---|
| 1. | 3,4 | 2,2-dimethylpropyl | phenylacetyl | 110–115 |

-continued

| No. | Substituents position (Ring B) | R¹ | Q | m.p. (°C.) |
|---|---|---|---|---|
| 2. | 3,5 | t-butyl | phenylacetyl | 174–176 |
| 3. | 3,5 | 2,2-dimethyl-propyl | phenylacetyl | 132–134 |
| 4. | 3,5 | cyclopentyl-methyl | phenylacetyl | 100–105 (hydrate) |
| 5. | 3.5 | t-butyl | benzoyl | 200–202 |
| 6. | 3,4 | t-butyl | (p-fluorophenyl)-acetyl | 182–184 |

The above acetophenone derivative starting materials were themselves obtained by reaction of the appropriate 2-bromoacetophenone derivative and the appropriate N-benzylamino amides.

The following new 2-bromo-acetophenone derivatives were obtained from the corresponding acetophenones in a similar manner to that described for 2-bromo-3',4'-bis(pivaloyloxy)acetophenone in Example 1:

2-bromo-3',5'-bis(cyclopentylacetoxy)acetophenone, oil, NMR: δ(CDCl₃): 7.8–7.1 (3H, complex, aromatic protons), 4.45 (2H, singlet, —COC$\underline{H}_2$Br), 2.58 (4H, singlet, CH—C$\underline{H}_2$—CO), 2.4–2.1 (18H, complex, cyclopentyl ring protons);

2-bromo-3',5'-bis(pivaloyloxy)acetophenone, m.p. 112°–114° C.;

2-bromo-3',5'-bis(3,3-dimethylbutyryloxy)acetophenone, m.p. 37°–39° C.;

2-bromo-3',4'-bis(3,3-dimethylbutyryloxy)acetophenone, oil, NMR: δ(CDCl₃): 8.0–7.1 (3H, complex, aromatic protons), 4.42 (2H, singlet, —COC$\underline{H}_2$Br),

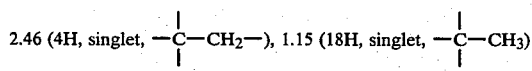

2.46 (4H, singlet, —C—CH₂—), 1.15 (18H, singlet, —C—CH₃)

The following new N-benzylamino amides required as starting materials were obtained in a similar manner to that described for N-[2-(benzylamino)ethyl]-2-phenylacetamide in Example 1:

N-[2-(benzylamino)ethyl]-benzamide, m.p. 54°–56° C., from ethyl benzoate;

N-[2-benzylamino)ethyl]-2-(p-fluorophenyl)acetamide, m.p. 194°–195° (hydrochloride), from ethyl phenylacetate.

EXAMPLE 5

N-[2-(Benzylamino)ethyl]-2-phenylacetamide (1.07 g.) was added to a solution of 2-bromo-3'-pivaloyloxymethyl-4'-pivaloyloxyacetophenone (0.83 g.) in dioxan (25 ml.). The solution was stirred at room temperature for 16 hours and then heated to 80° C. for 5 minutes. After dilution with ether (150 ml.) the solution was washed successively with 10% sodium carbonate solution, water and saturated brine. The ethereal solution was dried over (MgSO₄) filtered and evaporated to give crude 2-[N-benzyl-N-[2-(2-phenylacetamido)ethylamino]-3'-pivaloyloxymethyl-4'-pivaloyloxy-acetophenone as an oily residue, which was dissolved in methanol (25 ml.). Sodium borohydride (150 mg.) was added in portions to the methanolic solution cooled at −10° C. The mixture was stirred for 1 hour and then acidified to pH 4–5 by addition of glacial acetic acid. The methanol was removed by evaporation and the residue was suspended in water (50 ml.) and basified to pH 9–10 by addition of 2 N ammonia solution. The aqueous solution was then extracted with ether (3×50 ml.) and the combined extracts were dried (MgSO₄) and evaporated. The residue was dissolved in ethanol (50 ml.) and the solution was hydrogenated in the presence of 10% palladium-carbon (50 mg.) at atmospheric pressure and room temperature during 24 hours. After separation of catalyst, the solution was evaporated to give 1-[3-pivaloyloxymethyl-4-pivaloyloxyphenyl]-2-[2-(2-phenylacetamido)ethylamino]ethanol as an oil. The oil was dissolved in the minimum quantity of isopropyl acetate and the solution acidified to pH 4–5 by dropwise addition of methane sulphonic acid. The methanesulphonic acid salt of 1-[3-pivaloyloxymethyl-4-pivaloyloxyphenyl]-2-[2-(2-phenylacetamido)ethylamino]ethanol was thus obtained in 24% yield as a gum which was crystallised from isopropyl acetate and had m.p. 105°–107° C.

EXAMPLE 6

In a similar manner to that described in Example 3 for 1-[3,4-bis(pivaloyloxy)phenyl]-2-[2-(2-phenylacetamido)ethylamino]ethanol, there was obtained from 3'-pivaloyloxymethyl-4'-pivaloyloxyphenylglyoxal and N-(2-aminoethyl)-2-phenylacetamide, 1-[3-pivaloyloxyphenyl-4-pivaloxyphenyl]-2-[2-(2-phenylacetamido)ethylamino]ethanol as its methane sulphonate salt, m.p. 105°–107° C.

The glyoxal derivative used as starting material was obtained as follows:

3'-Pivaloyloxymethyl-4'-pivaloyloxyphenylglyoxal was obtained in a similar manner to that described in Example 3 for 3',4'-bis(pivaloyloxy)phenylglyoxal, but starting from 2-bromo-3'-pivaloyloxymethyl-4'-pivaloyloxyacetophenone except that the reaction mixture was left for 6 days rather than 18 hours at room temperature. The glyoxal had the following NMR: δ(DMSO-d₆) 1.1 (9H, singlet —C—C$\underline{H}_3$), 1.3 (9H, singlet —C—C$\underline{H}_3$), 6.7–8.0 (complex, aromatic $\underline{H}$), 8.3 (singlet —COC$\underline{H}$O).

EXAMPLE 7

Using a similar procedure to that described in Example 2, the following diesters of the formula:

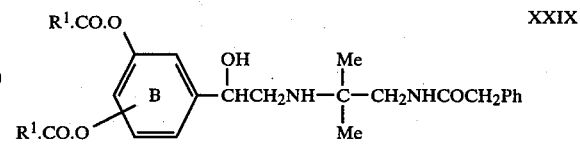

XXIX were obtained in yields of 45–80% (as their hydrobromide salts) by reduction of the corresponding acetophenone derivatives of the formula:

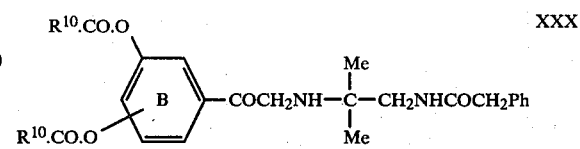

XXX with an excess of sodium borohydride, followed by catalytic hydrogenation in the presence of a stoichiometric amount of benzyl bromide to produce the hydrogen bromide salt in situ:

| Compound No. | Substituents position (Ring B) | R^10 | m.p. (°C.) |
|---|---|---|---|
| 1 | 3,4 | i-Pr | foam* |
| 2 | 3,4 | 1-ethylpropyl | 70–75 |
| 3 | 3,4 | t-Bu | 134–136 |
| 4 | 3,4 | 2,2-dimethylpropyl | 105–111 |
| 5 | 3,4 | 1-(2-methylpropyl)-3-methylbutyl | 79–82 |
| 6 | 3,4 | 1-methyl-2,2-dimethylpropyl | 109–110 |
| 7 | 3,4 | Ph | 113–117 (decomp.) |
| 8 | 3,4 | 4-MeO—Ph | 168–170 |
| 9 | 3,4 | i-Bu | 80–85 |
| 10 | 3,5 | t-Bu | 173–175 |
| 11 | 3,5 | 1-methyl-2,2-dimethylpropyl | 150–152 |
| 12 | 3,5 | 4-MeO—Ph | 140–145 |
| 13 | 3,5 | cyclopentylmethyl | 160–162 |
| 14 | 3,5 | 2,2-dimethylpropyl | 124–127 |
| 15 | 3,5 | i-Pr | 106–110 |

*Isolated as a foam, having NMR: δ(DMSO) 7.4–7.1 (8H, complex, aromatic protons); 5.0 (1H, complex, CH.OH); 3.6–3.0 (6H, complex, CH$_2$NH and CH$_2$CONH) 3.0–2.6 (2H, complex, >CHCO); 1.26, 1.20 (18H, two singlets, (CH$_3$)$_2$CH and —NHC(CH$_3$)$_2$—).

The necessary ketone starting materials of formula XXX were obtained by acylation of the appropriate phenol derivative of the formula:

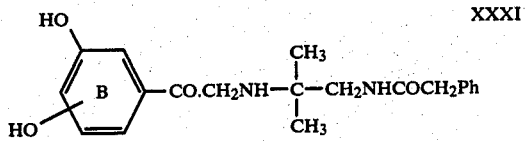

XXXI as its hydrobromide, by reaction with the appropriate acyl chloride or bromide of the formula R$^{10}$.CO.Cl or R$^{10}$.CO.Br. This acylation is illustrated by the following preparation of the acetophenone intermediate for compound 10 hereinabove:

Pivaloyl chloride (1.85 ml.) was added to a suspension of 2-[1,1-dimethyl-2-(2-phenylacetamido)ethyl]amino-3',5'-dihydroxyacetophenone (1.8 g.) in trifluoroacetic acid (10 ml.). The mixture was stirred at room temperature for 5 minutes, and then heated under reflux for 45 minutes. The reaction mixture was then evaporated and the oily residue was triturated with ether (100 ml.) and ethanol (1 ml.). The subsequently obtained mixture was then cooled for 18 hours at 0°–5° C. to give a precipitate of 2-[1,1-dimethyl-2-(2-phenylacetamido)ethyl]amino-3',5'-bis(pivaloyloxy)acetophenone trifluoroacetate (1.3 g.), m.p. 155°–156° C.

Using a similar procedure, the following acetophenone derivatives of formula XXX were obtained in yields of 30–70% as their trifluoroacetate salts:

| Intermediate for Compound No. | Substituents position (Ring B) | R^10 | m.p. (°C.) |
|---|---|---|---|
| 1 | 3,4 | i-Pr | 136–138 |
| 2 | 3,4 | 1-ethylpropyl | 140–142 |
| 3 | 3,4 | t-Bu | 205–208 |
| 4 | 3,4 | 2,2-dimethylpropyl | 112–115 |
| 5 | 3,4 | 1-(2-methylpropyl)-3-methylbutyl | 130–135 |
| 6 | 3,4 | 1-methyl-2,2-dimethylpropyl | 190–194 |
| 7 | 3,4 | Ph | 110–111 |
| 8 | 3,4 | 4-MeO—Ph | 125–130 |
| 9 | 3,4 | i-Bu | 140–141 |
| 11 | 3,5 | 1-methyl-2,2-dimethylpropyl | 195–200 |
| 12 | 3,5 | 4-MeO—Ph | 90–95 (decomp.) |
| 13 | 3,5 | cyclopentylmethyl | 175–178 |
| 14 | 3,5 | 2,2-dimethylpropyl | 148–154 |
| 15 | 3,5 | i-Pr | 175–180 |

The phenol starting materials of formula XXXI were obtained as follows:

1. 2-[1,1-dimethyl-2-(2-phenylacetamido)ethyl]amino-3',4'-dihydroxyacetophenone:

A solution of 2-bromo-3',4'-bis(benzyloxy)acetophenone (5.24 g.) and N-(2-amino-2-methylpropyl)-2-phenylacetamide (5.5 g.) in dioxan (25 ml.) was stirred for 2 hours at room temperature. The reaction mixture was diluted with dry ether (200 ml.) and the precipitate of N-(2-amino-2-methylpropyl)-2-phenylacetamide hydrobromide was separated by filtration. The ethereal filtrate was washed with water (3×50 ml.), brine (100 ml.) dried (MgSO$_4$) and then a fresh solution of saturated ethereal hydrogen bromide was added until the solution was just acid. After 18 hours at 0°–5° C. the precipitate which had formed was collected to give 2-[1,1-dimethyl-2-(2-phenylacetamido)ethyl]amino-3',4'-bis(benzyloxy)acetophenone hydrobromide as a solid (6.85 g.) m.p. 155°–160° C. This hydrobromide (5.0 g.) was dissolved in absolute ethanol (300 ml.) and the solution was hydrogenated at atmospheric pressure using 10% w/w palladium-on-carbon (3.0 g.) as catalyst. When the uptake of hydrogen was complete (about 3 hours), the catalyst was removed by filtration and the ethanolic filtrate was evaporated at a temperature below 30° C. to give 2-[1,1-dimethyl-2-(2-phenylacetamido)ethyl]amino-3',4'-dihydroxyacetophenone hydrobromide as a foam (3.7 g.) which was used directly for further acylation.

2. 2-[1,1-dimethyl-2-(2-phenylacetamido)ethyl]amino-3',5'-dihydroxyacetophenone:

This compound was obtained as a foam suitable for further acylation and in 98% yield, by a similar procedure but starting from 2-bromo-3',5'-bis(benzyloxy)acetophenone and N-(2-amino-2-methylpropyl)-2-phenylacetamide, and with intermediate isolation of 2-[1,1-dimethyl-2-(2-phenylacetamido)ethyl]amino-3',5'-bis(benzyloxy)acetophenone hydrobromide, m.p. 150°–153° C.

The N-(2-amino-2-methylpropyl)-2-phenylacetamide was obtained as follows:

A solution of 1,1-dimethylethylenediamine (8.8 g.) in ether (250 ml.) was added during 2 hours to a stirred solution of phenylacetyl chloride (15.4 g.) in ether (250 ml.). The mixture was further stirred at room temperature for 2 hours. The solid was separated by filtration, and dissolved in warm water (150 ml.). The solution obtained was filtered. The filtrate was basified by addition of an excess of saturated aqueous sodium carbonate solution (50 ml.), and then extracted with chloroform (3×250 ml.). The extracts were dried (MgSO$_4$) and evaporated to give an oil which crystallised on addition of a 1:1 v/v mixture of ether and petrol (60°–80° C.) to give N-(2-amino-2-methylpropyl)-2-phenylacetamide (13.1 g.), m.p. 68°–71° C. (after recrystallisation from aqueous ethanol.)

EXAMPLE 8

Using a similar procedure to that described in Example 2 the following diesters of the formula:

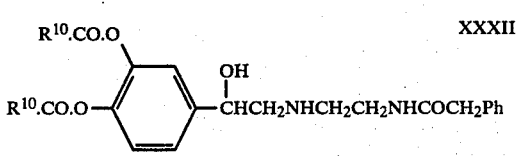

were obtained in yields of 30–65% (as their hydrobromide salts) by reduction of the corresponding acetophenone derivative of the formula:

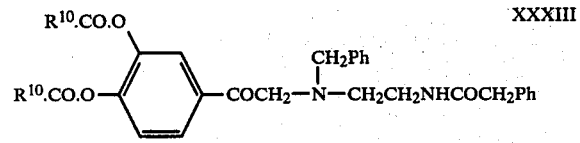

with an excess of sodium borohydride to give an alcohol of the formula:

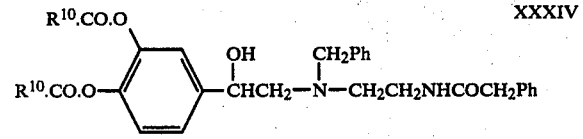

which was then hydrogenolysed in the presence of benzyl bromide to give the hydrogen bromide salt in situ:

| Compound No. | $R^{10}$ | m.p. (°C.) |
|---|---|---|
| 1 | n-Pr | 102–104 |
| 2 | i-Pr | 116–117 |
| 3 | heptyl | oil(a) |
| 4 | i-Bu | 124–128 |
| 5 | 1-ethylpropyl | 102–105 |
| 6 | 1-(2-methylpropyl)-3-methylbutyl | 98–105 |
| 7 | 1-methyl-2,2-dimethylpropyl | 111–114 |
| 8 | 1-ethyl-2,2-dimethylpropyl | oil(b) |
| 9 | 1,1-diethylpropyl | foam(c) |
| 10 | Ph | oil(d) |
| 11 | 4-Me—Ph | foam(e) |
| 12 | 4-MeO—Ph | oil(f) |

Notes (a)isolated as an oil: NMRδ: 9.0–8.5 (2H, broad, $\overset{+}{N}H_2$); 8.32 (1H, broad, NHCO); 7.5–7.1 (8H, singlet, aromatic protons); 5.0 (1H, doublet, CHOH); 3.6–2.8 (complex, CH$_2$NH and CH$_2$CONH); 2.5 (4H, multiplet, CH$_3$(CH$_2$)$_5$CH$_2$CO); 1.8–1.0 (20H, complex, CH$_3$(CH$_2$)$_5$CH$_2$CO); 0.88 (6H, broad triplet, CH$_3$(CH$_2$)$_5$CH$_2$CO), (b)isolated as an oil: NMRδ 9.0–8.5 (2H, broad, $\overset{+}{N}H_2$); 8.3 (1H, broad, NHCO); 7.6–7.0 (8H, complex, aromatic protons); 5.05 (1H, doublet, CHOH), 3.6–2.7 (6H, complex, CH$_2$NH and CH$_2$CONH); 2.26 [2H, triplet (J 7 c/s), CH—CO], 1.65 [4H, triplet (J 7 c/s), CH$_2$—CH—CO]; 1.04 (18H, singlet, (CH$_3$)$_3$ C); 0.9 (6H, triplet, CH$_3$CH$_2$).

(c)isolated as a foam: NMRδ: 8.9–8.5 (2H, complex, $\overset{+}{N}H_2$); 8.35 (1H, complex, NHCO); 7.4–7.1 (8H, complex, aromatic protons); 5.0 (1H, doublet, CHOH); 3.6–2.8 (8H, complex, CH$_2$NH and CH$_2$CONH); 1.85–1.20 [12H, complex, (CH$_3$CH$_2$)$_3$C.CO]; 1.1–0.5 [18H, complex, (CH$_3$CH$_2$)$_3$C.CO];

(d)isolated as an oil: NMRδ: 9.0–8.6 (2H, broad $\overset{+}{N}H_2$); 8.4 (1H, broad, NHCO); 8.1–7.1 (18H, complex, aromatic protons); 5.1 (1H, doublet, CHOH); 3.6–2.9 (complex, CH$_2$NH and CH$_2$CONH);

(e)isolated as a foam; NMRδ: 9.0–8.5 (2H, broad, $\overset{+}{N}H_2$); 8.38 (1H, broad, NHCO); 8.0–7.0 (16H, complex, aromatic protons); 5.06 (1H, doublet, CHOH); 3.6–2.8 (8H, complex, CH$_2$NH and CH$_2$CONH) 2.34 (6H, singlet, 4-CH$_3$—Ph);

(f)isolated as an oil: NMRδ: 8.35 (1H, broad, NHCO); 8.0–6.8 (16H, complex, aromatic protons); 5.2 (1H, doublet, CH.OH); 3.8 (6H, singlet, 4-CH$_3$O—Ph); 3.7–2.9 (8H, complex, CH$_2$NH and CH$_2$CONH).

The necessary ketone starting materials of formula XXXIII were obtained in a similar manner to those of formula XXX in Example 7 by acylation of 2-{N-benzyl-N-[2-(2-phenylacetamido)ethyl]amino}-3',4'-dihydroxyacetophenone hydrobromide, either using the appropriate acyl halide in trifluoroacetic acid solution (Method A, as described in Example 7), or using a mixture of the acyl chloride, the corresponding alkanoic or aroic acid, and hydrogen chloride (Method B).

Method B is illustrated by the following preparation of the intermediate for compound 1 hereinabove:

A mixture of 2-{N-benzyl-N-[2-(2-phenylacetamido)ethyl]amino}-3',4'-dihydroxyacetophenone hydrobromide (1.0 g.) and butyric acid (6 ml.) was saturated at room temperature with gaseous hydrogen chloride during 3 minutes. Butyryl chloride (6 ml.) was then added and the mixture was stirred at 90°–95° C. for 1.5 hours, giving a clear solution after about 5 minutes. The solution was then concentrated to half volume by evaporation under reduced pressure and the residue was diluted with ether (25 ml.) to give 2-{N-benzyl-N-[2-(2-phenylacetamido)ethyl]amino}-3',4'-bis(butyryloxy)acetophenone hydrochloride as a solid precipitate (0.65 g.), m.p. 115°–117° C.

Using either of these methods with the appropriate acyl halides, the following ketone derivatives of formula XXXIII were obtained in yields of 35–75% as their trifluoroacetate salt (Method A) or hydrochloride salt (Method B):

| Intermediate for Compound No. | $R^{10}$ | Acylation Method | m.p. (°C.) |
|---|---|---|---|
| 2 | i-Pr | B | 115–117 |
| 3 | heptyl | A | oil (a) |
| 4 | i-Bu | B | foam (b) |
| 5 | 1-ethylpropyl | A | oil (c) |
| 6 | 1-(2-methylpropyl)-3-methylbutyl | A | foam (d) |
| 7 | 1-methyl-2,2-dimethylpropyl | A | oil (e) |
| 8 | 1-ethyl-2,2-dimethylpropyl | A | oil (f) |
| 9 | 1,1-diethylpropyl | A | oil (g) |
| 10 | Ph | A | 173–176 |
| 11 | 4-Me—Ph | A | 155–160 |

| Intermediate for Compound No. | R¹⁰ | Acylation Method | m.p. (°C.) |
|---|---|---|---|
| 12 | 4-MeO—Ph | A | 149–154 |

Notes:
(a) isolated as an oil: NMRδ: 8.55 (1H, broad, NHCO); 8.0–7.0 (8H, complex, aromatic protons); 5.05 (2H, broad); 4.4 (2H, broad); 3.8–3.0 (complex, CH₂CO and CH₂NH); 2.5 [4H, multiplet, CH₃(CH₂)₅CH₂CO]; 1.8–1.0 [20H, complex CH₃(CH₂)₅CH₂CO]; 0.85 [6H, triplet, CH₃(CH₂)₅CH₂CO];
(b) isolated as a foam of satisfactory purity as judged by IR spectroscopy and TLC (thin layer chromatography) analysis;
(c) isolated as an oil: NMRδ: 8.45 (1H, broad triplet, NHCO); 8.0–7.1 (8H, complex, aromatic protons); 4.95 (2H, singlet); 4.36 (2H, singlet); 3.8–3.0 (complex, CH₂CO and CH₂NH); 2.5 (DMSO + 2H, complex, >CHCO); 1.65 [8H, quartet, (CH₃CH₂)₂CHCO]; 0.98 [12H, triplet, (CH₃CH₂)₂CHCO];
(d) isolated as a foam: NMRδ: 8.5 (1H, broad, NHCO); 8.0–7.0 (8H, complex, aromatic protons); 4.95 (2H, singlet); 4.38 (2H, singlet); 4.2–3.0 (complex, CH₂NH and CH₂CO); 2.4–1.7 (DMSO + ester >CH—) (24H, multiplet, CH₃);
(e) isolated as an oil: NMRδ: -9.50 (1H, broad, NH); 8.50 (1H, broad, NHCO); 8.0–7.0 (8H, complex, aromatic protons); 5.05 (2H, singlet, PhCH₂N); 4.40 (2H, singlet, COCH₂N); 3.6–3.0 (complex, NCH₂CH₂NH); 2.5 [complex, —CH(CH₃)CO—]; 1.15 (6H, doublet, —CH(CH₃)CO—
(f) isolated as an oil: NMRδ: -8.50 (1H, broad, NHCO); 8.0–7.0; (8H, complex, aromatic protons); 5.05 (2H, singlet, PhCH₂N); 4.40 (2H, singlet, COCH₂N); 3.6–3.0 (complex, NCH₂CH₂NH); 2.3 [2H, triplet, CH₃CH₂.CH(CH₃)₂.CO]; 2.0–1.2 [complex, CH₃CH₂.CH(CH₃)₂.CO]; 1.04 and 0.9 [24H, singlet and triplet CH₃CH₂.CH(CH₃)₂.CO];
(g) isolated as an oil of satisfactory purity as judged by IR and TLC analysis.

The required phenol starting material was prepared as follows:

3′,4′-Bis(acetoxy)-2-bromoacetophenone was reacted with N-[2-(benzylamino)ethyl]-2-phenylacetamide using a similar procedure to that described in Example 1 for the analogous pivaloyloxy derivative to give 2-{N-benzyl-N-[2-(2-phenylacetamido)ethyl]amino}-3′,4′-bis-(acetoxy)acetophenone, which was isolated as its free base and converted to its hydrochloride salt with ethereal hydrogen chloride to give a solid, m.p. 140°–145° C.

This hydrochloride salt was dissolved in methanol containing 2% v/v of hydrobromic acid, and the solution was heated under reflux for 2 hours. After cooling to room temperature, the solution was diluted with ether (100 ml.) and stored at 0°–5° C. to give 2-{N-benzyl-N-[2-(2-phenylacetamido)ethyl]amino}-3′,4′-dihydroxyacetophenone hydrobromide as a white solid in 98% yield, m.p. 175°–177° C. (after recrystallisation from methanol/ether).

EXAMPLE 9

Using a similar procedure to that described in Example 2 the following esters of the formula:

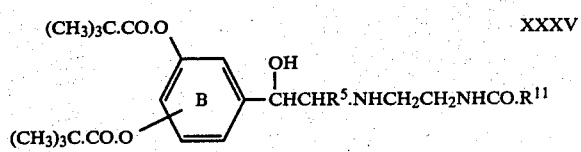

XXXV were obtained (as their hydrobromide salts) in yields of 30–85% by reduction of the corresponding acetophenone derivatives of the formula:

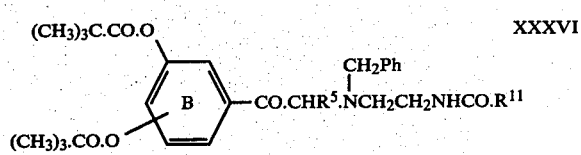

XXXVI with an excess of sodium borohydride to give an alcohol of the formula:

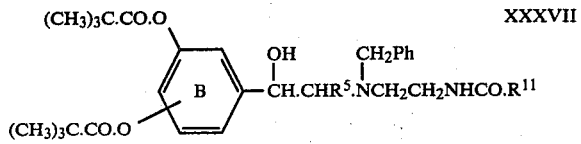

XXXVII which was then hydrogenolysed in the presence of benzyl bromide to give the hydrogen bromide salt in situ:

| Compound No. | Substituents position (Ring B) | R⁵ | R¹¹ | m.p. (°C.) |
|---|---|---|---|---|
| 1 | 3,4 | H | 4-Cl—Ph | 102–104 |
| 2 | 3,4 | H | 4-MeO—Ph | foam (a) |
| 3 | 3,4 | H | 4-F—PhCH₂ | 174–175 |
| 4 | 3,4 | H | 4-MeO—PhCH₂ | 105–108 |
| 5 | 3,4 | H | 4-Cl—PhCH₂ | 156–158 |
| 6 | 3,4 | H | Ph.CHMe | 79–86 |
| 7 | 3,4 | H | Ph.O.CH₂ | 162–165 |
| 8 | 3,4 | H | 3-CF₃—Ph.O.CH₂ | 80–81 |
| 9 | 3,4 | H | Ph | 166–169 |
| 10 | 3,5 | H | 4-MeO—PhCH₂ | oil (b) |
| 11 | 3,4 | Me | Ph.CH₂ | 134–136 |

Notes:
(a) isolated as a foam: NMRδ(CDCl₃): 8.1 (1H, broad, NHCO); 8.0–6.6 (7H, complex, aromatic protons); 5.3 (1H, broad, CHOH); 3.7 (3H, singlet, 4-CH₃O—Ph); 3.8–2.9 (complex, CH₂NH); 1.28 [18H, singlet, (CH₃)₃C];
(b) isolated as an oil: NMRδ(CDCl₃): 9.1–8.5 (2H, broad, NH₂); 8.4 (1H, broad singlet, NHCO); 7.5–6.6 (7H, complex, aromatic protons); 3.7 (3H, singlet, 4-CH₃O—Ph); 3.9–2.7 (complex, CH₂NH and CH₂CONH); 1.28 [18H, singlet, (CH₃)₃C.]

the starting acetophone derivative of formula XXXVI had the following properties (as their hydrobromide salts):

| Intermediate for Compound No. | Substituents position (Ring B) | R⁵ | R¹¹ | m.p. (°C.) |
|---|---|---|---|---|
| 1 | 3,4 | H | 4-Cl—Ph | 210–212 |
| 2 | 3,4 | H | 4-MeO—Ph | 210–211 |
| 3 | 3,4 | H | 4-F—Ph.CH₂ | 182–184 |
| 4 | 3,4 | H | 4-MeO—Ph.CH₂ | sticky solid(a) |
| 5 | 3,4 | H | 4-Cl—Ph.CH₂ | 175–178 |
| 6 | 3,4 | H | Ph.CHMe | 168–170 |
| 7 | 3,4 | H | Ph.O.CH₂ | foam(b) |
| 8 | 3,4 | H | 3-CF₃—Ph.O.CH₂ | 148–150 |
| 9 | 3,4 | H | Ph | 200–202 |
| 10 | 3,5 | H | 4-MeO—Ph.CH₂ | 123–126 |
| 11 | 3,4 | Me | Ph.CH₂ | 214–215 |

Notes
(a)isolated as a sticky soild: NMRδ: 8.65 (H, broad, NHCO); 8.1–6.8 (7H, complex aromatic protons); 5.2 (2H, singlet, PhCH₂N); 4.5 (2H, singlet, N.CO.CH₂); 3.7 (3H, singlet, OCH₃); 3.9–3.1 (complex); 1.3 [18H singlet, (CH₃)₃C]
(b)isolated as a foam: NMRδ: 8.35 (1H, groad, NHCO); 8.0–6.7 (8H, complex aromatic protons); 5.15 (2H, singlet, PhCH₂N); 4.65 (2H, singlet, PhOCH₂); 4.35 (2H, singlet, N.CO.CH₂); 4.0–3.0 (complex, NCH₂CH₂NH); 1.28 [18H, singlet (CH₃)₃C].

The acetophenone derivatives of formula XXXVI obtained in yields of 25–55% using an analogous procedure to that used for 2-{N-benzyl-N-[2-(2-phenylacetamido)ethyl]amino}3′,4′-bis(pivaloyloxy)acetophenone hydrobromide in Example 1, by reacting 2-bromo-3′,4′- or 3′,5′-bis(pivaloyloxy)acetophenone [or for compound No. 11, 2-bromo-3′,4′-bis(-pivaloyloxy)propiophenone] with the appropriate N-benzyl-N¹-acylethylene diamine of the formula:

PhCH$_2$NHCH$_2$CH$_2$NHCOR$^{11}$    XXXVIII

These ethylene diamine derivatives were obtained in an analogous manner to that described in Example 1 for N-benzyl-N$^1$(phenylacetyl)ethylene diamine (required for compound No. 11) and had the following properties (hydrochloride salts):

| Starting material for Compound No. | R$^{11}$ | m.p. (°C.) |
|---|---|---|
| 1 | 4-Cl—Ph | 234-236 |
| 2 | 4-MeO—Ph | 198-200 |
| 3 | 4-F—Ph.CH$_2$ | 194-195 |
| 4,10 | 4-MeO—Ph.CH$_2$ | 196-197 |
| 5 | 4-Cl—Ph.CH$_2$ | 54-55* |
| 6 | Ph.CHMe | syrup (a) |
| 7 | Ph.O.CH$_2$ | 182-184 |
| 8 | 3-CF$_3$—Ph.O.CH$_2$ | 147-149 |
| 9 | Ph | 54-56* |

*m.p. of free base
(a) isolated as a syrup: NMR (free base)δ: 7.5-7.0 (10H, complex, aromatic protons); 5.95 (1H, broad, NHCO); 3.65 (2H, singlet, PhCH$_2$N); 3.55 (1H, multiplet, CHCH$_3$); 3.25 (2H, multiplet, CH$_2$NHCO); 2.63 (2H, triplet, PhCH$_2$NHCH$_2$); 1.6 (1H, PhCH$_2$NH); 1.48 (3H, doublet, CHCH$_3$).

The 2-bromo-3',4'-bis(pivaloyloxy)propiophenone required for compound No. 11 was obtained as follows:

3',4'-Bis(pivaloyloxy)propiophenone was first prepared as a mobile liquid (63.6 g.), in a similar manner to 3',4'-bis(pivaloyloxy)acetophenone in Example 1, starting from 3',4'-dihydroxypropiophenone (40 g.), pivaloylchloride (63.3 ml.) and triethylamine (73.2 ml.). This mobile liquid (40.1 g.) was then reacted with bromine (7.2 ml.) in a similar manner to that used in Example 1 to obtained 2-bromo-3',4'-bis(pivaloyloxy)acetophenone. The crude bromo compound thus obtained was purified by dry column chromatography on silica gel as described in Example 1 to give pure 2-bromo-3',4'-bis(pivaloyloxy)propiophenone as a solid (18.4 g.), m.p. 58°-60° C.

EXAMPLE 10

A suspension of 2-[1,1-dimethyl-2-(2-phenoxyacetamido)ethylamino]-3',4'-bispivaloyloxy acetophenone trifluoroacetate (3.3 g.) in propan-2-ol (25 ml.) was cooled to −10° C. and sodium borohydride (0.56 g.) was added in two portions interspersed by a portion of methanol (10 ml.). After 45 minutes at −10° C., a saturated aqueous solution (50 ml.) of sodium chloride was added and the mixture was extracted with ether (3×80 ml.). Evaporation of the dried (MgSO$_4$) ethereal extracts gave 1-[3,4-bis(pivaloyloxy)phenyl]-2-[1,1-dimethyl-2-(2-phenoxyacetamido)amino]ethanol as the free base (3.2 g.) which was dissolved without purification in ethanol (50 ml.). To this ethanol solution was added benzyl bromide (0.6 ml.) and the mixture was then hydrogenated in the presence of 10% palladium-on-carbon (0.5 g.) at atmospheric pressure and room-temperature during 3 hours. The catalyst was separated by filtration through kieselguhr. The residue was washed with ethanol (20 ml.) and the combined ethanol filtrate and washings were evaporated. The residue obtaned was triturated with ether (200 ml.) to give 1-[3,4-bis(pivaloyloxy)phenyl]-2-[1,1-dimethyl-2-(2-phenoxyacetamido)ethylamino]ethanol hydrobromide (2.1 g.), m.p. 156°-158° C. (after crystallisation from ethanol-ether).

In a similar manner, except that the benzyl bromide was replaced by an equivalent amount of benzyl chloride, the corresponding hydrochloride was obtained as a solid, m.p. 129°-32° C.

The starting 2-[1,1-dimethyl-2(2-phenoxyacetamido)ethylamino]-3',4'-bis(pivaloyloxy)acetophenone trifluoroacetate was obtained in an analogous manner to that for the corresponding 2-(2-phenylacetamido)ethylamino compound to Example 7, as a solid, in 85% yield, m.p. 183°-185° C., by acylation of 2-[1,1-dimethyl-2(2-phenoxyacetamido)ethylamino]-3',4'-dihydroxyacetophenone with pivaloyl chloride in trifluoroacetic acid.

The starting 2-[1,1-dimethyl-2-(2-phenoxyacetamido)ethylamino]-3',4'-dihydroxyacetophenone was itself obtained as a foam, of satisfactory purity for acylation, by hydrogenolysis of 2-[1,1-dimethyl-2-(2-phenoxyacetamido)ethylamino]-3',4'-bis(benzyloxy)acetophenone hydrobromide in an analogous manner to that described for 2-[1,1-dimethyl-2-(2-phenylacetamido)ethylamino]-3',4'-bis(benzyloxy)acetophenone hydrobromide in Example 7.

The starting 3',4'-bis(benzyloxy)acetophenone derivative was also prepared in 67% yield by analogy with the corresponding compound in Example 7 from 2-bromo-3',4'-bis(benzyloxy)acetophenone and N-(2-amino-2-methylpropyl)-2-phenoxyacetamide, and had m.p. 137°-139° C.

The N-(2-amino-2-methylpropyl)-2-phenoxyacetamide may be prepared in an analogous manner to that described for N-(2-amino-2-methylpropyl)-2-phenylacetamide in Example 3 or 7, and had m.p. 55°-56° C., after recrystallisation from aqueous ethanol.

EXAMPLE 11

In a similar manner to Example 2, -[3,4-bis(-pivaloyloxy-2-chlorophenyl]-2-[2-(2-phenylacetamido)ethylamino]ethanol hydrobromide and 1-[3,4-bis(isovaleryloxy)-2-chlorophenyl]-2-[2-(2-phenylacetamido)ethylamino]ethanol hydrobromide as solids, in yields of 56 and 41%, and having m.p. 139°-142° C. and 128°-131° C. respectively, from 2-{N-benzyl-N[2-(2-phenylacetamido)ethyl]amino}-2'-chloro-3',4'-bis(pivaloyloxy)- or -3',4'-bis(isovaleryloxy)-acetophenone trifluoroacetate.

The necessary starting trifluoroacetates were obtained as oily solids in 70-85% yield (which solids were suitable for use without purification in the above process) by reaction of 2-{N-benzyl-N[2-(2-phenylacetamido)ethyl]amino}-2'-chloro-3',4'-dihydroxyacetophenone hydrobromide with pivaloyl or isovaleryl chloride in trifluoroacetic acid, in a similar manner to that described in Example 7.

The 2'-chloro-3',4'-dihydroxy acetophenone derivative was obtained as follows:

An ethereal diazomethane solution was directly distilled into a mixture of 3,4-bis(benzyloxy)-2-chlorobenzoyl chloride (25.0 g.) in ether (200 ml.) maintained at −25° C. The reaction mixture was then allowed to warm up to room temperature and stirred at this temperature for 4 hours. A saturated ethereal solution of hydrogen bromide (approximately 150 ml.) was then added cautiously to the reaction mixture until nitrogen evolution ceased. Chromatographic silica gel (125 g.) was then added and the mixture was evaporated. The residue was added to the top of a column of dry chromatographic silica-gel (900 g.) (previously deactivated by addition of 10% v/w water and then equilibrated with 10% v/w of a 5% v/v solution of ethyl acetate in toluene). The column was then developed by fractional elution, first with the same solvent mixture (1.1 l.), and then with ethyl acetate (1.5 l.). Evaporation of the appropriate ethyl acetate fractions (as monitored by thin layer chromatography) gave 2-bromo-3',4'-bis(benzyloxy)-2'-chloroacetophenone as a solid (28.1 g.), m.p. 94°–96° C.

The ethereal diazomethane solution was obtained using a standard procedure by adding a solution of N-methyl-N-nitroso toluenesulphonamide (45.0 g.) in ether (300 ml.) dropwise to a stirred solution of potassium hydroxide (12.9 g.) in water (21 ml.), maintaining the reaction temperature at 50°–55° C., and the addition rate to balance the loss of ethereal diazomethane by distillation.

[The starting benzoyl chloride was obtained in 90% yield from (2-chloro-3,4-bis(benzyloxy)benzoic acid by reaction with thionyl chloride in a conventional manner and had m.p. 124°–126° C. The 2-chloro-3,4-bis(benzyloxy)benzoic acid was itself obtained in 80% yield as a solid, m.p. 159°–162° C., by oxidation of 2-chloro-3,4-bis(benzyloxy)benzaldehyde (itself described by Kaiser et alia in *J. Medicinal Chemistry* 1974, 17, 1071) with chromium trioxide in sulphuric acid solution (Jones reagent)].

A mixture of 2-bromo-3',4'-bis(benzyloxy)-2-chloroacetophenone (2.95 g.) and N-[2-(benzylamino)ethyl]-2-phenylacetamide (3.7 g.) in dioxan (20 ml.) was stirred at room temperature for 3 hours. The reaction mixture was diluted with dry ether (200 ml.) and the precipitate, N-[2-(benzylamino)ethyl]-2-phenylacetamide hydrobromide, was separated by filtration. The filtrate was washed with water (3×50 ml.) and then brine (100 ml.) dried (MgSO4), filtered, and a fresh solution of hydrogen bromide in ether added until the pH was just acid. The mixture was stored for 16 hours at 0°–5° C. and the oily solid which formed was triturated with a mixture of ethanol and ether to give 2-{N-benzyl-N[2-(2-phenylacetamido)ethyl]amino}-2'-chloro-3',4'-bis(benzyloxy)acetophenone hydrobromide (4.2 g.), m.p. 162°–164° C.

This hydrobromide (0.6 g.) was stirred for 4 hours at room temperature with a solution of hydrogen bromide in acetic acid (48% w/v; 3 ml.) to give a solution. This solution was evaporated and the residue was triturated with a mixture of ether and ethanol to give 2-{N-benzyl-N[2-(2-phenylacetamido)ethyl]amino}-2'-chloro-3',4'-dihydroxy-acetophenone hydrobromide (0.45 g.), m.p. 196°–197° C.

EXAMPLE 12

In a similar manner to Example 10, 1-[3,4-bis(pivaloyloxy)-2-chlorophenyl]-2-[1,1-dimethyl-2-(2-phenoxyacetamido)ethylamino]-ethanol hydrobromide and 1-[3,4-bis(isovaleryloxy)-2-chlorophenyl]-2-[1,1-dimethyl-2-(2-phenoxyacetamido)ethylamino]ethanol hydrobromide were obtained as solids in 58% and 49% yield and having m.p. 163°–164° C. and 176°–179° C. respectively, from 2-{[1,1-dimethyl-2-(2-phenoxyacetamido)ethyl]amino}-2'-chloro-3',4'-bis(pivaloyloxy)- or -3',4'-bis(isovaleryloxy)acetophenone trifluoroacetate.

The necessary trifluoroacetates were obtained as oily solids in yields of 70–80% (which solids were used in the above process without purification) in an analogous manner to that described in Example 7, by reacting 2-{[1,1-dimethyl-2-(2-phenoxyacetamido)ethyl]amino}-2'-chloro-3',4'-dihydroxy acetophenone hydrobromide (A) with pivaloyl or isovaleryl chloride in trifluoroacetic acid.

The above acetophenone derivative (A) was itself prepared in 85% yield, as a solid m.p. 141°–143° C. by a similar procedure to that described for the equivalent starting material in Example 11, but from 2-{[1,1-dimethyl-2-(2-phenoxyacetamido)ethyl]amino}-2'-chloro-3',4'-bis(benzyloxy)acetophenone hydrobromide. The latter compound was itself obtained in 40% yield as a solid, m.p. 61°–63° C., from N-(2-amino-2-methylpropyl)-2-phenoxyacetamide and 2-bromo-3',4'-bis(benzyloxy)acetophenone using a procedure similar to that in Example 11.

EXAMPLE 13

A solution of 3'-acetoxymethyl-4'-acetoxyphenylglyoxal hydrate (1.45 g.) and N-(2-amino-2-methylpropyl)-2-phenylacetamide (1.04 g.) in acetonitrile (50 ml.) was stirred at room temperature for 30 minutes. Acetic acid (2 ml.), followed by sodium cyanoborohydride (0.64 g.), was added to the vigorously stirred mixture. Stirring was continued at room temperature for 16 hours. The mixture was then evaporated. The semi-solid residue was partitioned between ethyl acetate (100 ml.) and 10% v/v aqueous acetic acid (100 ml.). The organic phase was separated, dried (MgSO4), filtered and evaporated. The residual oil was purified on a column of chromatographic silica gel (150 g.) using 10% v/v ethanol/chloroform as eluant. The appropriate fractions from the column [as monitored by TLC (SiO2:10% v/v ethanol/chloroform)] were combined and evaporated to give 1-[3-acetoxymethyl-4-acetoxyphenyl]-2-[1,1-dimethyl-2-(2-phenylacetamido)ethyl amino]ethanol as an oil (0.9 g., 36%): NMR δ(CDCl3): 7.8–6.9 (8H, complex, aromatic protons), 6.3–5.8 (2H, broad singlet, CH(OH)CH2 and CH2NHC(CH3)2) 5.0 (3H, broad singlet, COOCH2 and CH(OH)CH2) 3.5 (2H, sharp singlet, PhCH2CO), 3.35–3.2 (2H, doublet, (CH3)2CCH2NH). 3.05–2.8 (2H, CH(OH)CH2NH complex), 2.25 (3H, sharp singlet, CH3COO) 2.0 (3H, sharp singlet, CH3COOCH2) 1.2 (6H, doublet, NHC(CH3)2CH2); and pure by TLC (SiO2: 10 or 20% v/v ethanol/chloroform).

The starting substituted phenylglyoxal was itself prepared as follows:

3'-Chloromethyl-4'-hydroxyacetophenone (108 g.) was added to a mixture of anhydrous sodium acetate (54 g.) glacial acetic acid (500 ml.) and acetic anhydride (250 ml.). The mixture was heated at 95° C. for 4 hours, then concentrated by distilling under reduced pressure. The gummy residue was dissolved in water (500 ml.) and the aqueous solution was extracted with chloroform (3×300 ml.). The combined extracts were dried (MgSO4), filtered and evaporated to give a yellow oil. This was distilled under high vacuum to give 3'-acetoxymethyl-4'-acetoxyacetophenone as a colourless viscous liquid (108 g.), b.p. 143°–147° C. (0.3 mm.), which crystallised on cooling to give solid, m.p. 47°–48° C.

A solution of bromine (7.1 g.) in chloroform (20 ml.) was added dropwise to a stirred solution of 3'-acetoxymethyl-4'-acetoxyacetophenone (11.0 g.) in chloroform (150 ml.) at room temperature. After completion of the addition, the solution was washed with water (2×150 ml.) and brine (100 ml.). The organic phase was dried (MgSO4), filtered and evaporated to give 3'-acetoxymethyl-4'-acetoxy-2-bromoacetophenone (10.0 g.) which was judged to be sufficiently pure by IR and TLC [SiO2; 1:1 v/v EtOAc/petrol (60°–80° C.)] for use without further purification or characterisation. A solution of 3'-acetoxymethyl-4'-acetoxy-2-bromoacetophenone (10.0 g.) in dimethylsulphoxide (150 ml.) was stirred at room temperature for 48 hours. The solution was then poured into ice-water (500 ml.) and extracted with ethyl acetate (3×200 ml.). The organic layers were combined, dried (MgSO4) filtered. The solvent was removed by evaporation to give 3'-acetoxymethyl-4'-acetoxy-phenylglyoxal hydrate as a yellow oil (6.5 g. 81%). The glyoxal derivative had a satisfactory IR spectrum and was judged pure by TLC ($SiO_2$: EtOAc) and was therefore used without full characterisation or isolation.

EXAMPLES 14-15

Using a similar procedure to that described in Example 13 the following diesters were obtained in yields of 50-70% as oils, pure by TLC ($SiO_2$: 10 or 20 v/v ethanol/chloroform):

1(3'-isovaleryloxymethyl-4'-isovaleryloxyphenyl)-2-[1,1-dimethyl-2-(2-phenylacetamido)ethylamino]ethanol (Example 14)

NMR $\delta(CDCl_3)$: 7.5-7.0 (8H, complex, aromatic protons);
6.8-6.6 (2H, broad singlet, CH(OH)CH2 and CH2NHC(CH3)2);
5.0 (3H, broad singlet, $CO_2CH_2$ and CH(OH)CH2);
3.5 (2H, sharp singlet, PhCH2CO);
3.4 (2H, broad doublet, (CH3)2C.CH2NH);
3.2-2.8 (2H, complex, CH(OH)CH2NH);
2.3 (2H, doublet, $CH_2CO_2$);
2.1 (2H, doublet, $CH_2CO_2CH_2$);
1.2 (6H, doublet, NHC(CH3)2CH2);
1.1-0.8 (12H, 2 doublets, (CH3)2.CH);

1(3'-valeryloxymethyl-4'-valeryloxyphenyl)-2-[1,1-dimethyl-2-(2-phenylacetamido)ethylamino]ethanol (Example 15)

NMR $\delta(CDCl_3)$: 7.5-7.0 (8H, complex, aromatic protons);
6.4-6.1 (2H, broad singlet, CH(OH)CH2 CH2NHC(CH3)2);
5.0 (3H, broad singlet, $CO_2CH_2$ CH(OH)CH2);
3.6 (2H, broad doublet, PhCH2CO);
3.4 (2H, broad doublet, C(CH3)2CH2NH);
3.2-2.8 (2H, complex, CH(OH)CH2NH);
2.6 (2H, triplet, CH3(CH2)2CH2CO2);
2.2 (2H, triplet, CH3(CH2)2CH2CO2CH2);
1.8-1.2 (8H, complex, CH3CH2CH2CH2CO2);
1.2 (6H, doublet, NH-C(CH3)2CH2);
1.1-0.8 (6H, overlapping triplets, CH3(CH2)3CO2).

The starting substituted phenylglyoxals were obtained in a similar manner to that described for the phenylglyoxal derivative in Example 13 starting from the appropriate 2-bromoacetophenone. They were obtained as their hydrates, and were oils which were sufficiently pure, as judged by TLC (EtOAc: $SiO_2$) and IR spectroscopy, to be used in the above preparations without isolation and full characterisation.

The necessary 2-bromoacetophenones were obtained as follows:

1.
3'-Valerloxymethyl-4'-valeryloxy-2-bromoacetophenone (For Example 14)

Sodium hydride (2.0 g.) was added in portions to stirred valeric acid (150 ml.) over a period of 15 minutes. 3-Acetoxymethyl-4-acetoxy-acetophenone (40 gm.) was then added, and the mixture was heated to 160° C. and maintained at this temperature with stirring for 15 hours. The mixture was then concentrated by distilling under reduced pressure while maintaining the temperature at 160° C. The gummy residue was cooled and dissolved in ether (500 ml.). This solution was washed with 10% v/v sodium carbonate solution (3×250 ml.), water (2×500 ml.) and saturated brine (250 ml.). The organic phase was dried (MgSO4), filtered and evaporated to give a brown oil. This was distilled under high vacuum to give 3'-varleryloxymethyl-4'-valeryloxy-acetophenone as a colourless viscous liquid (16.0 g. 30%): NMR $\delta(CDCl_3)$:
7.9-7.0 (3H, 1,2,4 aromatic substitution pattern);
5.0 (2H, sharp singlet, $CO_2CH_2$);
2.5 (3H, sharp singlet, COCH3);
2.55-2.15 (4H, complex, CH3(CH2)2CH2CO2 and CH3(CH2)2CH2CO2CH2);
1.8-1.2 (8H, complex, CH3CH2CH2CH2CO2O);
1.1-0.8 (6H, overlapping triplets, CH3(CH2)3CO2).

A solution of bromine (4.2 g.) in chloroform (20 ml.) was added dropwise to a cooled stirred solution of 3'-valeryloxymethyl-4'-valeryloxyacetophenone (8.5 g.) in chloroform (100 ml.). During the addition, the temperature was maintained at 0°-5° C. by the addition of small pieces of solid carbon dioxide. The solution was then washed with 10% w/v sodium carbonate solution (3×100 ml.) water (2×100 ml.) and saturated brine (100 ml.). The organic phase was dried (MgSO4), filtered, and evaporated yielding 3'-valeryloxymethyl-4'-valeryloxy-2-bromoacetophenone (6 g., 57%), which was judged to be sufficiently pure by IR and TLC [$SiO_2$: 50 v/v EtOAc/petrol (60°-80°)] for use without further purification or characterisation.

2.
3'-Isovaleryloxymethyl-4'-isovaleryloxy-2-bromoacetophenone (For Example 15)

This compound was obtained using an analogous procedure to that described in (1) hereinabove, but using isovaleric instead of valeric acid in the first stage. The 2-bromoacetophenone derivative was isolated as an oil having a satisfactory IR spectrum and pure by TLC [$SiO_2$: 50% v/v EtOAc/petrol (60°-80°)]. The intermediate 3'-isovaleryloxymethyl-4'-isovaleryoxyacetophenone was also isolated as a liquid: NMR $\delta(CDCl_3)$:
7.9-7.0 (3H, 1,2,4 aromatic substitution pattern);
5.0 (2H, sharp singlet, $CO_2CH_2$);
2.5 (3H, sharp singlet, COCH3);
2.4 (2H, doublet, $CH_2CO_2$);
2.1 (2H, doublet, $CH_2CO_2CH_2$);
1.1-0.8 (12H, complex, (CH3)2CH).

EXAMPLE 16

In a similar manner to that described in Example 13 for 1-[3-acetoxymethyl-4-acetoxyphenyl]-2-[1,1-dimethyl-2-(2-phenylacetamido)ethylamino]ethanol, there was obtained from 3'-acetoxymethyl-4'-acetoxy-phenylglyoxal and N-(2-amino-2-methylpropyl)-2-phenoxyacetamide, 1-[3-acetoxymethyl-4-acetoxyphenyl]-2-[1,1-dimethyl-2-(2-phenoxyacetamido)ethylamino]ethanol, as an oil in 42% yield, having NMR $\delta(CDCl_3)$:
7.9-6.8 (8H, complex, aromatic protons);
6.2-5.6 (2H, broad singlet, CH(OH)CH2 and CH2NHC(CH3)2;
5.0, (2H, sharp singlet, CH3CO2CH2);

4.5, (2H, sharp singlet, PhOCH₂CO);
3.6–3.4 (2H, broad doublet, C(CH₃)₂CH₂NH);
3.3–2.8 (2H, complex, CH(OH)CH₂NH);
2.25 (3H, sharp singlet, CH₃CO₂);
2.0 (3H, sharp singlet, CH₃CO₂CH₂);
1.3 (6H, doublet, NHC(CH₃)₂CH₂);
and pure by TLC (SiO₂: 10 to 20% v/v ethanol/chloroform).

EXAMPLE 17

A solution of 1-(3,4-dihydroxyphenyl)-2-[1,1-dimethyl-2-(2-phenoxyacetamido)ethylamino]ethanol hydrobromide (0.8 g.) in trifluoroacetic acid (5.4 ml.) was treated with pivaloyl chloride (1.12 ml.) and the mixture was heated under reflux for 40 minutes. The mixture was then evaporated and the residue was dissolved in ether. The solution obtained was treated with ethereal hydrogen bromide until just acid, where upon an oily solid separated. Trituration of this material with ether (20 ml.) gave the triester, 1-[3,4-bis(pivaloyloxy)-phenyl]-2-[1,1-dimethyl-2-(2-phenoxyacetamido)ethylamino]ethyl pivaloate hydrobromide, as a solid (0.6 g.) m.p. 106°–110° C., NMR δ: 8.8 (2H, broad singlet, N+H₂); 8.45 (1H, triplet, NHCO); 7.8–6.8 (8H, complex, aromatic protons); 5.43 (1H, broad, =CH.O); 3.58 (2H, singlet, CH₂OPh); 4.0–3.0 (complex, CH₂NH; 1.3–1.2 (33H, broad singlet, C.CH₃).

The ethereal filtrate, after separation of solid triester, contained isolable amounts of the diester, 1-[3,4-bis(pivaloyoxy)phenyl]-2-[1,1-dimethyl-2(2-phenoxyacetamido)ethylamino]ethanol, identical with that produced in Example 10, as indicated by TLC on silica using the following solvent systems:
 (a) toluene/ethyl acetate/ethanol/ammonia (60/20/15/10, v/v)
 (b) toluene/ethanol/triethylamine (8/1/1, v/v)
 (c) ether/acetic acid/water (6/2/1, v/v)

The starting material was obtained as follows:
A suspension of 2[1,1-dimethyl-2-(2-phenoxyacetamido)ethyl]amino-3',4'-bis(benzyloxy)acetophenone hydrobromide (1.26 g.) in 2-propanol (10 ml.) was cooled to −10° C. and sodium borohydride (0.22 g.) was added in two portions interspersed by a a portion of methanol (10 ml.). The reaction mixture was allowed to warm to 10° C. After 30 minutes at this temperature, a saturated aqueous solution (100 ml.) of sodium chloride was added and the mixture was extracted with ether (3×100 ml.). The combined ether extracts were washed with water (100 ml.) and then brine (100 ml.), dried (MgSO₄) and evaporated to give 1-[3,4-bis(benzyloxy)-phenyl]-2-[1,1-dimethyl-2-(2-phenoxyacetamido)ethylamino]ethanol as a sticky residue (1.2 g.). This residue was dissolved in ethanol (30 ml.) and benzyl bromide (0.24 ml.) was then added. The mixture was hydrogenated at atmospheric pressure and temperature in the presence of 10% w/w palladium-on-carbon (0.4 g.) for 3 hours. The catalyst was separated by filtration, washed with ethanol (10 ml.) and the combined filtrate and washings evaporated to give 1-(3,4-dihydroxyphenyl)-2-[1,1-dimethyl-2-(2-phenoxyacetamido)ethylamino]ethanol hydrobromide as a foam (0.8 g.) having a satisfactory NRM spectrum and sufficiently pure for direct use in the above procedure.

EXAMPLE 18

Using a similar procedure to that described in Example 9, 1-[3,5-bis(pivaloyloxy)phenyl]-2-[2-(2-phenoxyacetamido)ethylamino]ethanol hydrobromide was obtained as a solid m.p. 93°–95° C. in 68% yield by reduction of 2-{N-benzyl-N-[2-(2-phenoxyacetamido)ethyl]amino}-3',5'-bis(pivaloyloxy)acetophenone hydrobromide (A) with an excess of sodium borohydride to give the corresponding alcohol of formula XXXVII in situ, which was then hydrogenolysed in the presence of benzyl bromide.

The acetophenone hydrobromide (A) was obtained as solid, m.p. 90°–110° C. having a satisfactory NMR spectrum, and in 43% yield, by reaction of 3',5'-bis(pivaloyloxy)-2-bromoacetophenone with N-[2-(benzylamino)ethyl]-2-phenoxyacetamide in similar manner to that described for the analogous starting material in Example 1.

EXAMPLE 19

A mixture of finely powdered 1-[3,4-bis(pivaloyloxy)phenyl]-2-[1,1-dimethyl-2-(2-phenoxyacetamido)ethylamino]ethanol hydrochloride or hydrobromide (0.5 parts by weight) in liquid paraffin (10 parts by weight) was added to molten white soft paraffin (89.5 parts by weight). The resulting mixture was allowed to cool to room temperature with fast stirring until a uniform ointment, suitable for application to humans, was formed.

In a similar manner, an ointment containing a compound of formula I as described in any one of Examples 1–9 or 11–18, or in a numbered part thereof, was obtained by using such a compound as the active ingredient in the above process.

EXAMPLE 20

A solution of 1-[3,4-bis(pivaloyloxy)phenyl]-2-[1,1-dimethyl-2-(2-phenoxyacetamido)ethylamino]ethanol hydrochloride or hydrobromide (0.1 parts by weight) in 2-propanol (30 parts by weight) was prepared. Water (66.9 parts by weight) was added and the mixture was stirred rapidly during the addition of "Carbopol" 940 (3 parts by weight) until a finely dispersed gel, suitable for application to humans, was formed.

In a similar manner, a gel containing a compound of formula I as described in any one of Examples 1–9 or 11–18, or in a numbered part thereof, was obtained by using such a compound as the active ingredient in the above process. *"Carbopol" 940 is a grade of carboxypolymethylene gelling agent, available from B. F. Goodison Chemical Co., Cleveland, Ohio, U.S.A. "Carbopol" is a trade mark.

EXAMPLE 21

A mixture of cetostearyl alcohol (9 parts by weight), liquid paraffin (7 parts by weight), sorbitan monostearate (2 parts by weight), polysorbate 60 (2 parts by weight) and finely powdered 1-[3,4-bis(pivaloyloxy)-phenyl]-2-[1,1-dimethyl-2-(2-phenoxyacetamido)ethylamino]ethanol hydrochloride or hydrobromide (0.1 parts by weight) was fused together at 65°–70° C. Water (79.9 parts by weight) was added with stirring to the melt thus obtained. The mixture was then stirred rapidly with slow cooling to room temperature until a homogeneous cream, suitable for application to humans, was obtained.

In a similar manner, a cream containing a compound of formula I as described in any one of Example 1–9 or 11–18 or in a numbered part thereof, was obtained by using such a compound as the active ingredient in the above process.

What we claim is:

1. An ester of the formula:

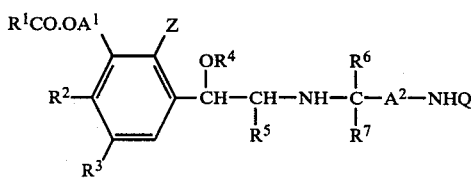

wherein $R^1$ is an isopropyl, t-butyl, isobutyl or (cyclopentyl)methyl radical; $R^2$ is a radical of the formula $R^1CO.O—$; $R^3$, $R^4$ an $R^5$ are hydrogen; $R^6$ and $R^7$ are both hydrogen or methyl radicals; $A^1$ is a direct bond; $A^2$ is a methylene radical; Z is hydrogen; and Q is a phenylacetyl, phenoxyacetyl or 2-phenylpropionyl radical; or a pharmaceutically-acceptable acid-addition salt thereof.

2. The ester 1-[3,4-bis(pivaloyloxy)phenyl]-2-[2-(2-phenylacetamido)ethylamino]-ethanol; 1-[3,4-bis(-pivaloyloxy)phenyl]-2-[1,1-dimethyl-2-(2-phenylacetamido)ethylamino]ethanol; 1-[3,4-bis(3,3-dimethylbutyryloxy)phenyl]-2-[2-(2-phenylacetamido)ethylamino]-ethanol; 1-[3,4-bis(-pivaloyloxy)phenyl-2-[2-(2-phenoxyacetamido)ethylamino]-ethanol or 1-[3,4-bis(isovaleryloxy)-phenyl]-2-[2-(2-phenylacetamido)ethylamino]-ethanol; or a pharmaceutically acceptable acid addition salt thereof.

3. The ester 1-[3,4-bis(pivaloyloxy)phenyl]-2-[1,1-dimethyl-2-(2-phenoxyacetamido)ethylamino]-ethanol; or a pharmaceutically acceptable acid-addition salt thereof.

4. A method for the topical treatment of an area of inflammation affecting the skin of a warm-blooded animal which comprises administering to said area of said animal requiring such treatment an effective amount of an ester of the formula:

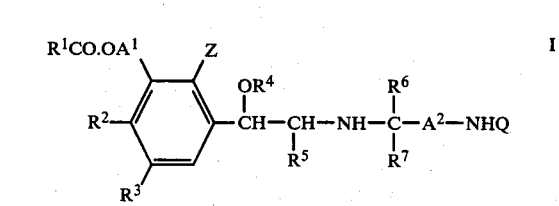

wherein $R^1$ is a $C_{1-11}$-alkyl or $(C_{3-6}$-cycloalkyl)-$C_{1-5}$-alkyl radical, or a phenyl or benzyl radical optionally bearing a $C_{1-6}$-alkyl or $C_{1-6}$-alkoxy radical as a nuclear substituent; one or $R^2$ and $R^3$ is hydrogen; the other of $R^2$ and $R^3$ is a radical of the formula $R^1CO.O—$ wherein $R^1$ has the meaning stated above; $R^4$ and $R^5$ are hydrogen; $R^6$ and $R^7$ are hydrogen, or methyl radicals; $A^1$ is a direct bond or a methylene radical; $A^2$ is a methylene radical; Z is hydrogen or chlorine; and Q is a radical of the formula:

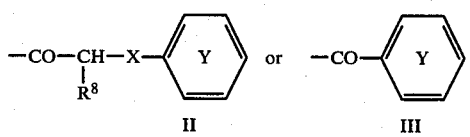

wherein $R^8$ is hydrogen or a methyl radical, X is a direct bond or oxygen, and benzene ring Y optionally bears a halogen atom, or trifluoromethyl, $C_{1-6}$-alkyl or $C_{1-6}$-alkoxy radical as a substituent; or a pharmaceutically acceptable acid-addition salt thereof.

5. The ester 1-[3,4-bis(pivaloyloxy)phenyl]-2-[2-(benzamido)-ethylamino]ethanol; or a pharmaceutically acceptable salt thereof.

* * * * *